Figure 1:
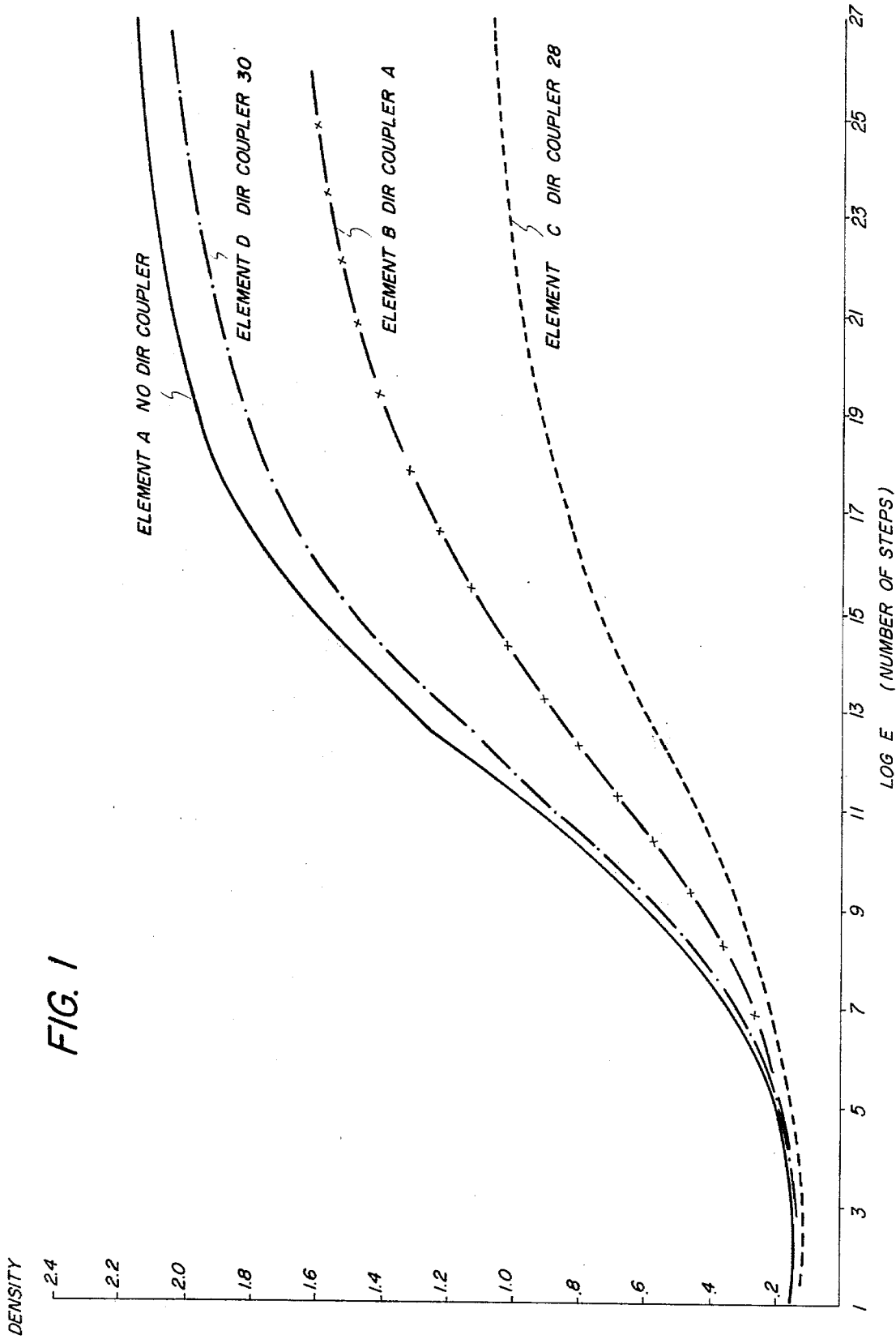
Figure 2:
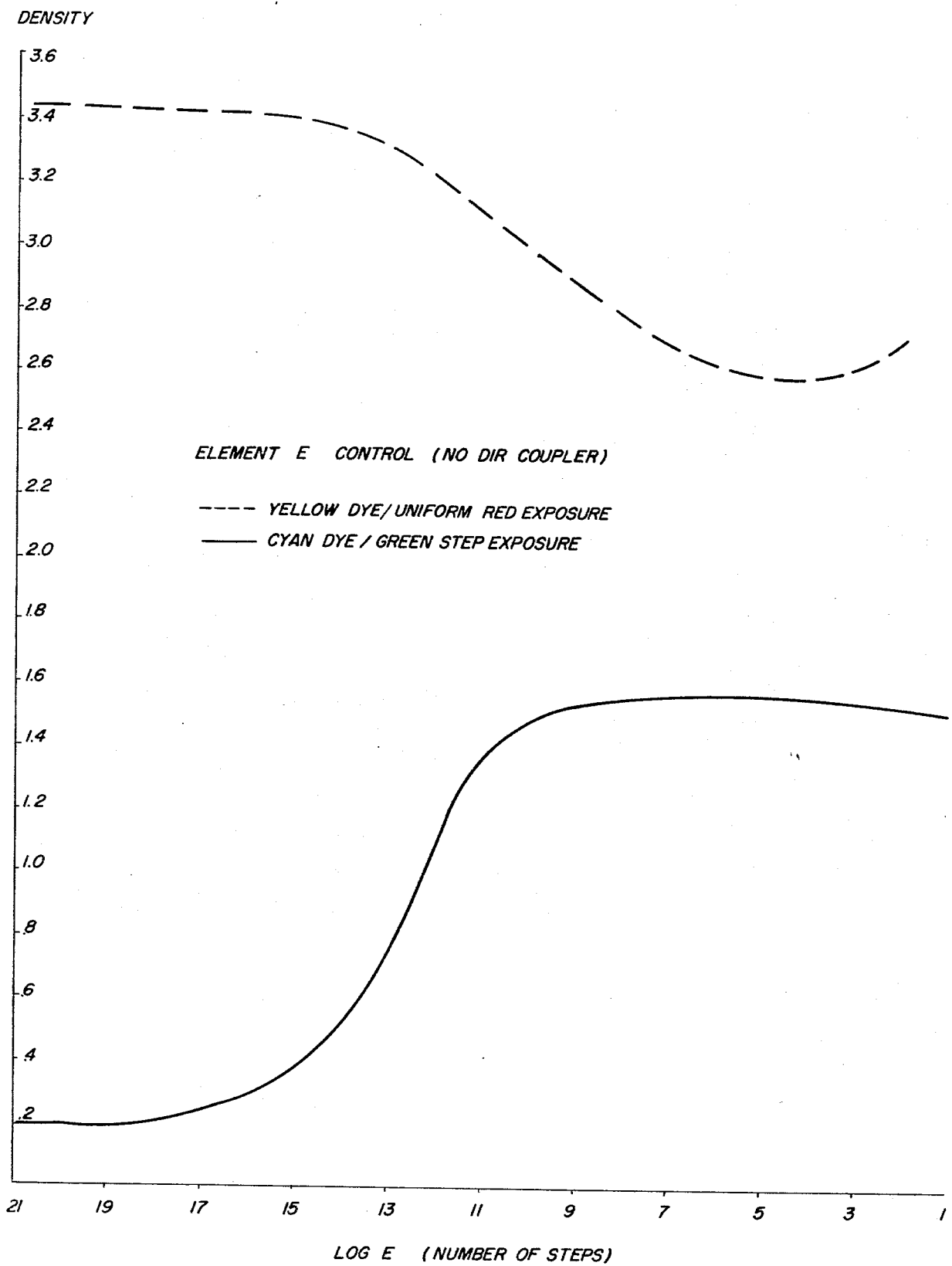
Figure 3:
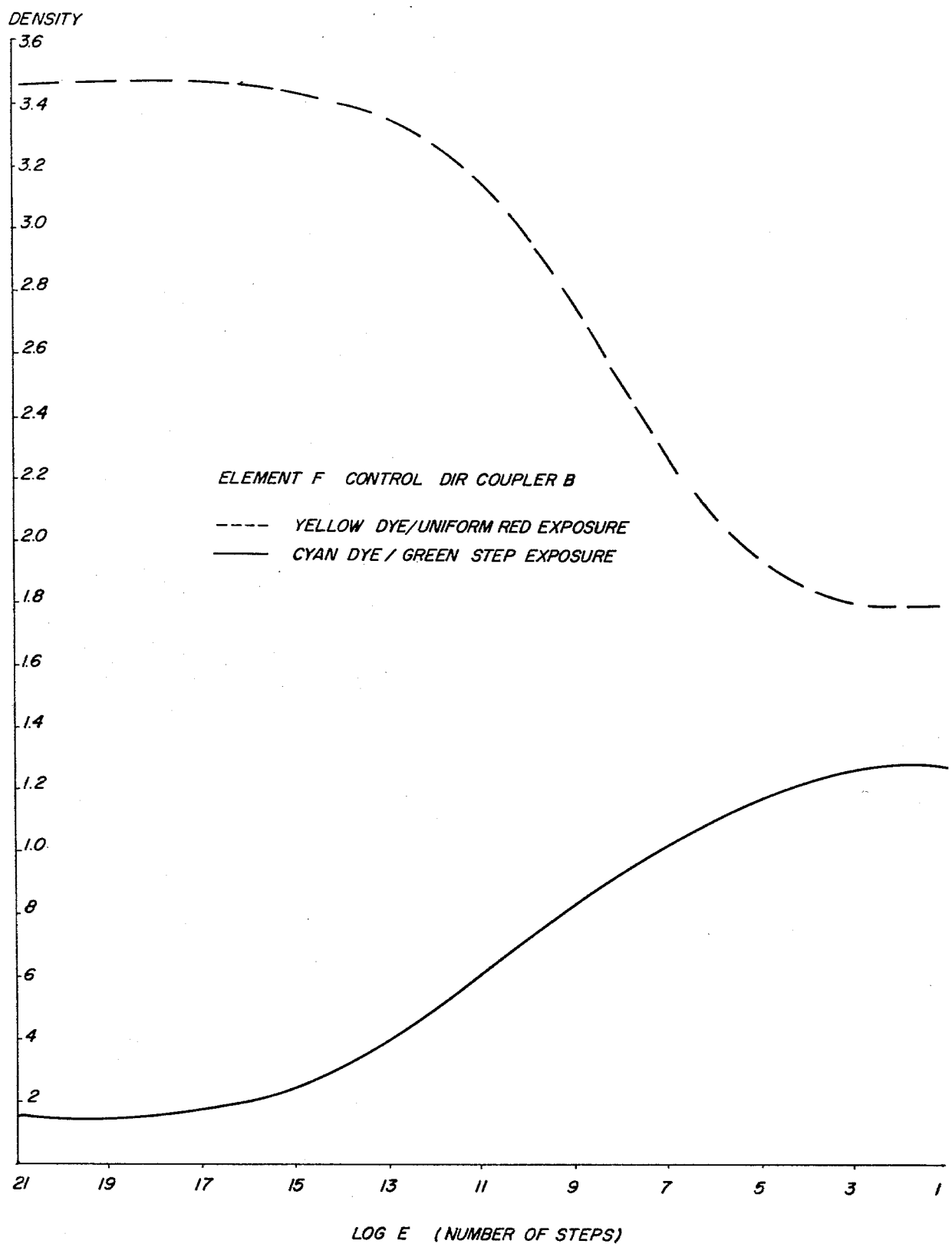
Figure 4:
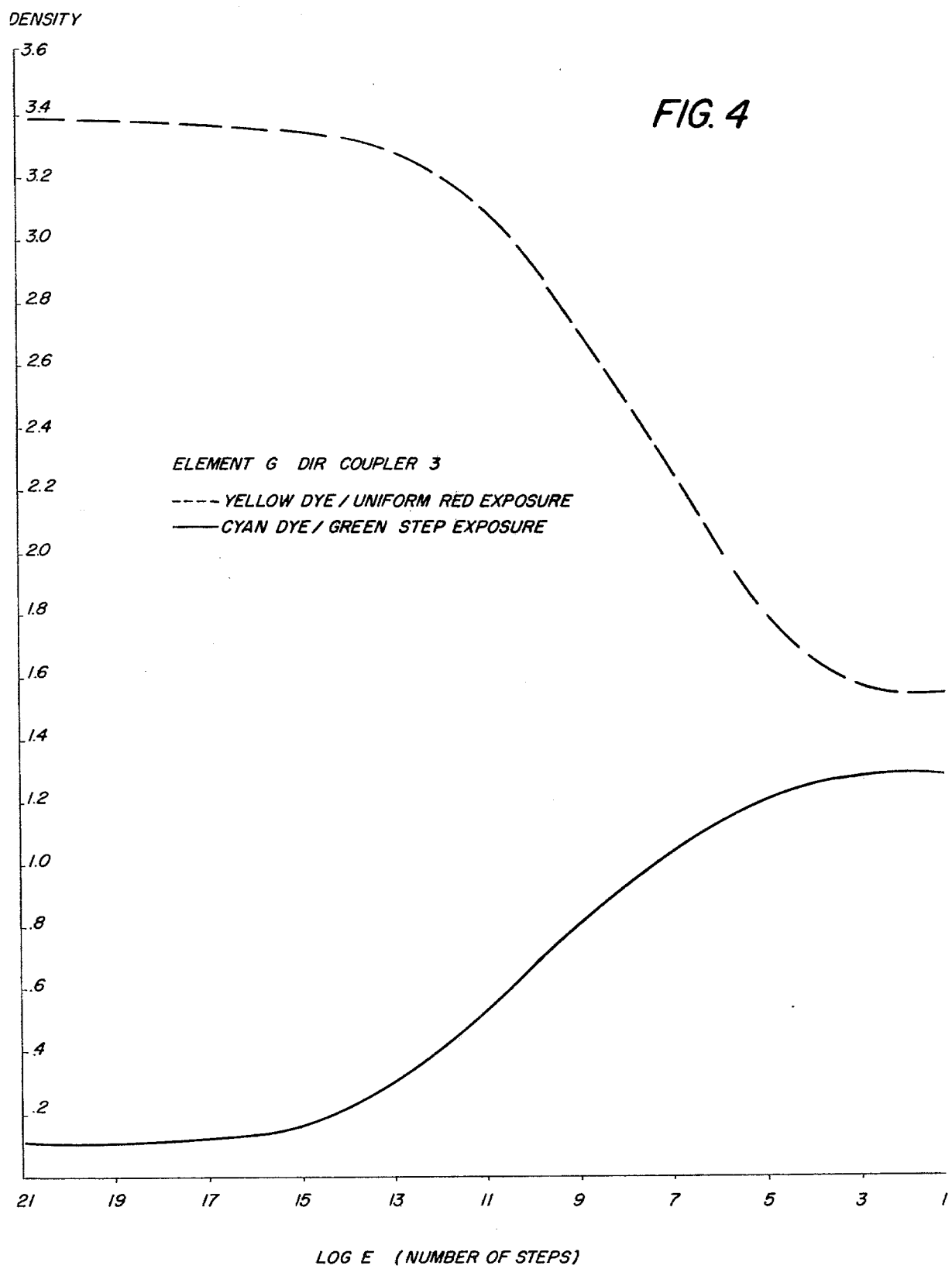
Figure 5:
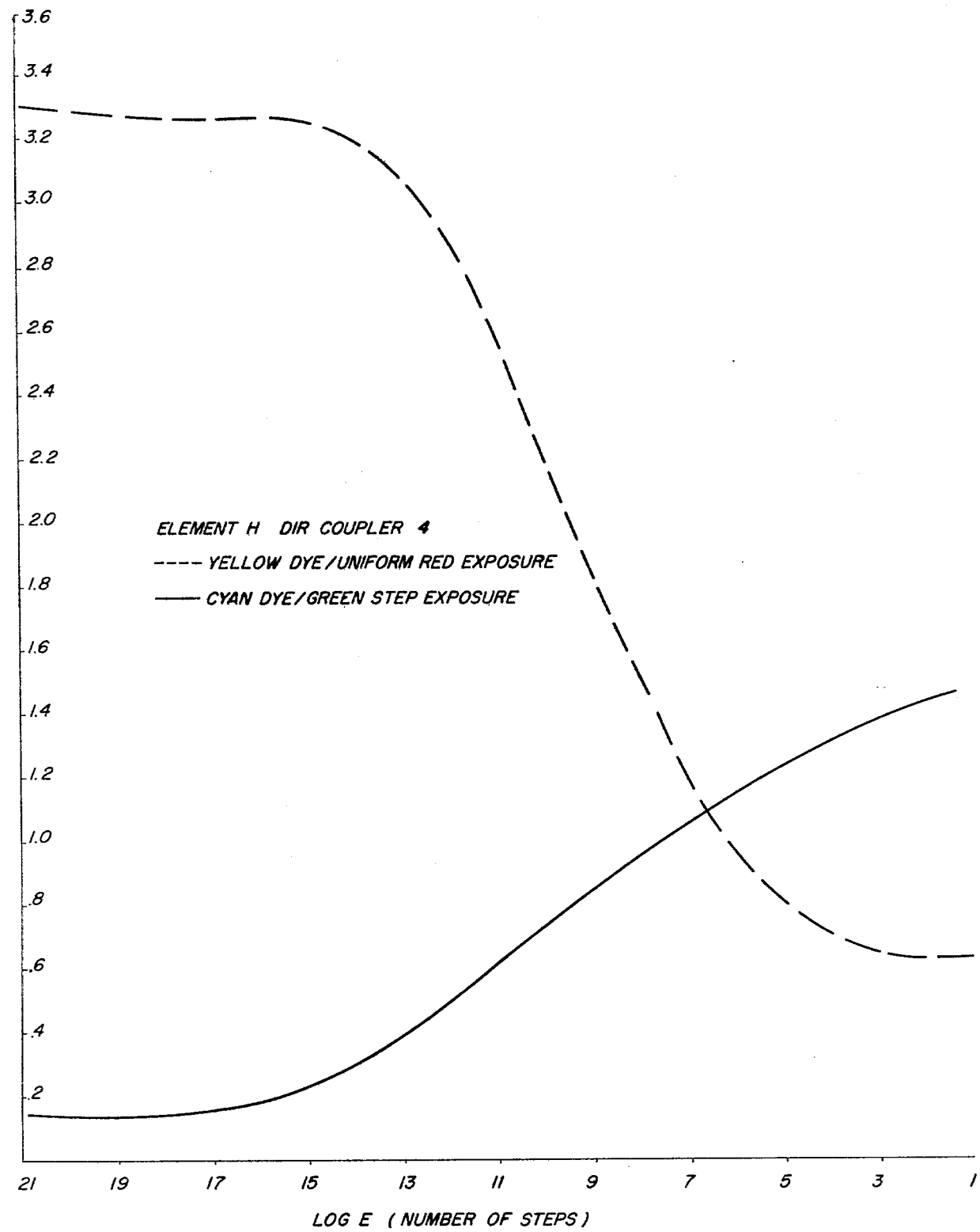
Figure 6:
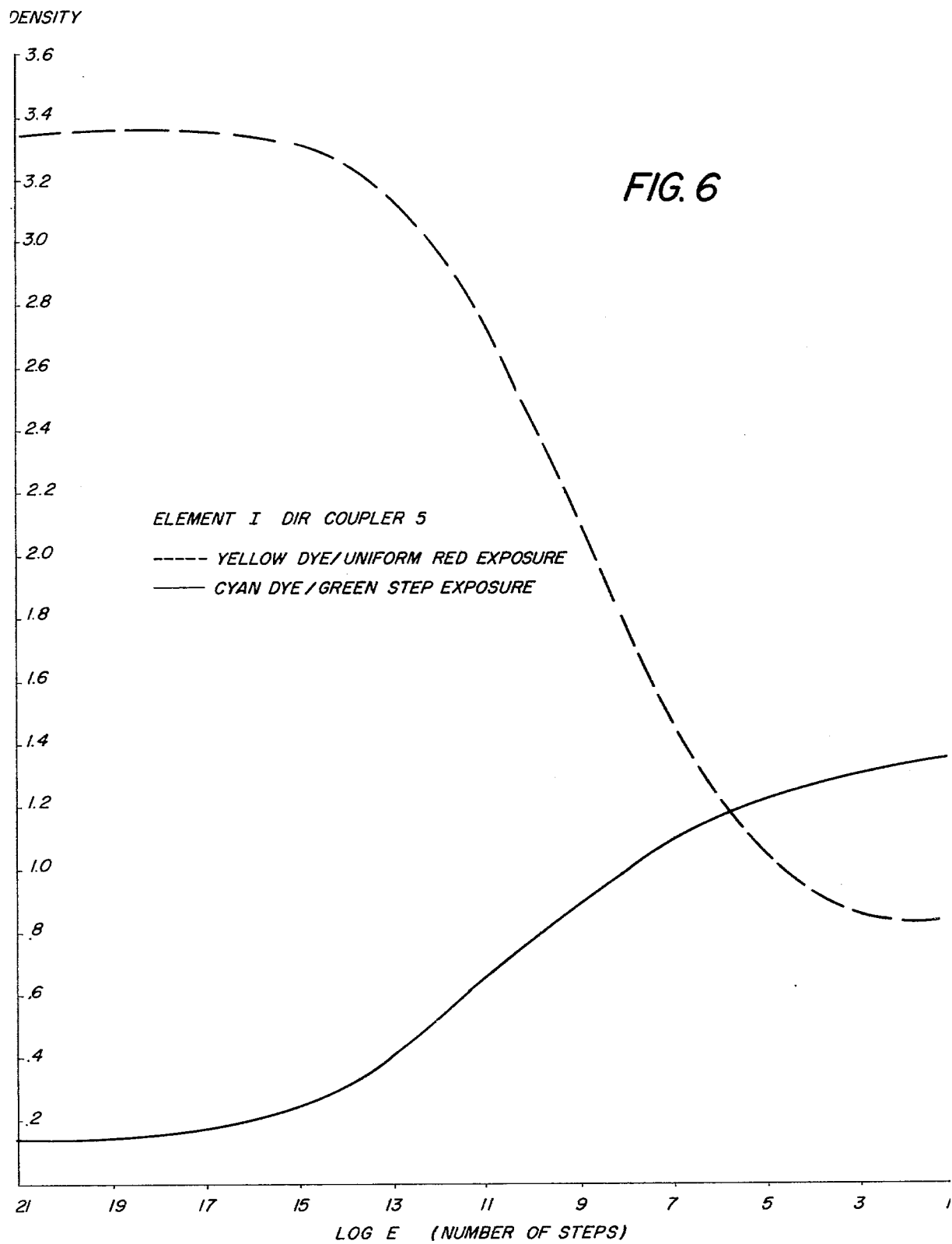

United States Patent [19]

Lau

[11] 4,248,962

[45] Feb. 3, 1981

[54] PHOTOGRAPHIC EMULSIONS, ELEMENTS AND PROCESSES UTILIZING RELEASE COMPOUNDS

[75] Inventor: Philip T. S. Lau, Rochester, N.Y.

[73] Assignee: Eastman Kodak Company, Rochester, N.Y.

[21] Appl. No.: 972,614

[22] Filed: Dec. 22, 1978

Related U.S. Application Data

[63] Continuation-in-part of Ser. No. 864,126, Dec. 23, 1977, abandoned.

[51] Int. Cl.$^3$ .......................... G03C 7/00; G03C 1/40
[52] U.S. Cl. ..................... 430/382; 430/362; 430/385; 430/387; 430/389; 430/390; 430/544; 430/548; 430/553; 430/555; 430/557; 430/558; 430/559; 430/957; 430/958
[58] Field of Search ............... 96/55, 56.5, 74, 100 R, 96/100 N, 77

[56] References Cited

U.S. PATENT DOCUMENTS

| | | | |
|---|---|---|---|
| 3,148,062 | 9/1964 | Whitmore et al. | 96/55 |
| 3,227,554 | 1/1966 | Barr et al. | 96/55 |
| 3,443,940 | 5/1969 | Bloom et al. | 96/77 |
| 3,516,831 | 6/1970 | Wolf et al. | 96/74 |
| 3,551,157 | 12/1970 | Salminen | 96/100 R |
| 3,644,498 | 2/1972 | Loria | 96/100 R |
| 3,647,452 | 3/1972 | Hendess et al. | 96/22 |
| 3,705,801 | 12/1972 | Holtz | 96/74 |
| 3,751,406 | 8/1973 | Bloom | 96/3 |
| 3,785,829 | 1/1974 | Fernandez | 96/100 R |
| 3,808,945 | 5/1974 | Matsuo et al. | 96/100 R |
| 3,880,658 | 4/1975 | Lestina et al. | 96/77 |
| 3,894,875 | 7/1975 | Cameron et al. | 96/100 R |
| 3,928,044 | 12/1975 | Arai et al. | 96/56.5 |
| 3,930,863 | 1/1976 | Shiba et al. | 96/74 |
| 3,935,016 | 1/1976 | Nishimura et al. | 96/95 |
| 3,942,987 | 3/1976 | Landholm et al. | 96/99 |
| 3,960,570 | 6/1976 | Oishi et al. | 96/55 |
| 3,980,479 | 9/1976 | Fields et al. | 96/100 R |
| 3,998,641 | 12/1976 | Schranz et al. | 96/100 R |
| 4,002,477 | 1/1977 | Bissonette | 96/77 |
| 4,002,480 | 1/1977 | Hinata et al. | 96/100 R |
| 4,012,258 | 3/1977 | Kojima et al. | 96/100 R |
| 4,139,379 | 2/1979 | Chasman et al. | 430/223 |
| 4,139,389 | 2/1979 | Hinshaw et al. | 430/223 |

OTHER PUBLICATIONS

Bordwell et al., JACS, vol. 79, p. 916, 1957.
Bender et al., JACS, vol. 80, p. 5380, 1958.
Bender, Chemical Reviews, vol. 60, pp. 53-113, 1960.
Gould, Mechanism and Structure in Organic Chemistry, Chapter 9, Holt, Rinehard and Winston, New York, 1959.
Fieser and Fieser, Organic Chemistry, pp. 517 and 518, Third Edition, Reinhold Publishing Co., New York, 1956.
Capon et al., *Neighboring Group Participation*, vol. 1, pp. 43-58, Plenum Press, New York, (1976).

*Primary Examiner*—Travis Brown
*Attorney, Agent, or Firm*—Joshua G. Levitt

[57] ABSTRACT

Photographic couplers which release a photographically useful group by an intramolecular nucleophilic displacement reaction can be used in photographic emulsions, elements and processes to provide a photographically useful group in a controlled manner.

63 Claims, 9 Drawing Figures

PHOTOGRAPHIC EMULSIONS, ELEMENTS AND PROCESSES UTILIZING RELEASE COMPOUNDS

This is a continuation-in-part of my copending application, Ser. No. 864,126 filed Dec. 23, 1977, now abandoned.

This invention relates to novel photographic compounds which release photographically useful groups during photographic processing and to photographic emulsions, elements and processes utilizing such compounds.

The a rt has recognized various ways in which a photographically useful group can be released from compounds in photographic elements and processes. For example, Whitmore et al U.S. Pat. No. 3,148,062 and Barr et al U.S. Pat. No. 3,227,554 show the release of a development inhibitor or a dye from the coupling position of a photographic coupler upon reaction of the coupler with oxidized color developing agent. Bloom et al U.S. Pat. No. 3,443,940 and Bloom U.S. Pat. No. 3,751,406 show a photographic coupler containing a dye in a non-coupling position. Reaction of the coupler with oxidized color developing agent followed by a ring closure reaction of the coupled developing agent at the point of attachment of the dye leads to release of the dye from the coupler. Holtz U.S. Pat. No. 3,705,801 shows photographic couplers which release from the coupling position thereof a bleach inhibitor upon reaction of the coupler with oxidized color developing agent. Fields et al U.S. Pat. No. 3,980,479 shows compounds containing a nucleophilic group and a photographically useful group attached to the compound through an electrophilic cleavage group. When subjected to alkaline conditions the nucleophilic group and the electrophilic cleavage group interact to release the photographically useful group unless the compound has reacted with oxidized developing agent, in which event release is inhibited. Hinshaw et al U.S. Patent Application Ser. No. 534,966 filed Dec. 20, 1974, Chasman et al U.S. Patent Application Ser. No. 775,025 filed Mar. 7, 1977 and Hinshaw et al U.S. Patent Application Ser. No. 775,219 filed Mar. 7, 1977 show other compounds from which a photographically useful group is released by a nucleophilic displacement reaction during photographic processing.

Thus, as can be seen from these representative patents, the prior art has used several techniques to release imagewise a variety of photographically useful groups to be employed for various purposes in photographic elements and processes. A feature which these compounds and techniques have in common is that the photographically useful group is released directly from the compound in its useful form. Such direct release limits control over the timing and rate of release of the photographically useful group, as well as over the rate and distance it may then travel through the element before reacting with another compound in the element. Some degree of control over these parameters may be obtained by suitably modifying one or more of: (1) the moiety from which the photographically useful group is released, (2) the means of attachment of the photographically useful group to the moiety from which it is released and (3) the photographically useful group itself. However, such modification may be inconsistent with the end use intended for the moiety or the photographically useful group and hence removes a degree of freedom in designing a compound for a given purpose. For example, modifying a photographic coupler containing a development inhibitor so as to modify the rate of release of the development inhibitor may affect not only rate of release but also may affect the hue of the dye formed by the coupler and/or the reactivity or diffusivity of the development inhibitor.

Thus, there is a need for compounds that will release or otherwise make available photographically useful groups, but which will permit control over such parameters as time of release, rate of release, and rate of diffusion of the photographically useful group, without modifying the photographically useful group or the coupler moiety from which it is released in a way which would be inconsistent with the ultimate use for which each is intended.

I have found that this can be accomplished by means of a photographic coupler containing a timing group which is displaced from the coupler as a result of reaction of the coupler with oxidized color developing agent and thereafter undergoes an intramolecular nucleophilic displacement reaction to release a photographically useful group.

One embodiment of my invention is the couplers as described above. Another embodiment of my invention is a process for forming photographic images by developing an exposed silver halide emulsion with a color developing agent in the presence of a coupler as described above. Other embodiments of my invention are silver halide emulsions and photographic elements containing couplers as described above.

Preferably, couplers of my invention contain a timing group between a coupler moiety and a photographically useful group, so that reaction of the coupler with oxidized color developing agent cleaves the bond between the timing group and the coupler, and then an intramolecular nucleophilic displacement reaction cleaves the bond between the photographically useful group and the timing group. Thus, the sequential cleavage of first the bond between the timing group and the coupler moiety, followed by cleavage of the bond between the photographically useful group and the timing group is a characteristic feature of compounds of this invention.

As used herein the terms "coupler" and "coupler compound" refer to the entire compound, including the coupler moiety, the timing group and the photographically useful group, while the term "coupler moiety" refers to that portion of the compound other than the timing group and the photographically useful group.

The particular timing group employed, including the linkage by which it is attached to the coupler moiety and the nature of the substituents on it, can be varied so as to control such parameters as rate and time of cleavage of the timing group from the coupler moiety and of the photographically useful group from the timing group. Since these parameters can be controlled by modification of the timing group, they need not be emphasized in selecting the particular coupler moiety and the particular photographically useful group, thus providing greater freedom in selecting such moieties and groups for a particular end use.

If the photographically useful group is joined to the coupler moiety only through the timing group, then cleavage of the bond between the timing group and the coupler moiety releases the timing group and the photographically useful group as a unit. In this embodiment the particular timing group employed, including the nature of the substituents on it, can additionally control the rate and distance of diffusion of the unit formed by the timing group and the photographically useful group after this unit is released from the coupler moiety but before the photographically useful group is released from the timing group. If the photographically useful group is joined to the coupler moiety both directly and through the timing group, the particular timing group and the nature of the substituents on it can control the rates of cleavage of the timing group from the coupler and from the photographically useful group, and, hence, can control the rate at which the photographically useful group is released. In this embodiment the direct linkage between the photographically useful group and the coupler moiety prevents diffusion of the photographically useful group.

In one embodiment, my invention relates to a photographic coupler containing a timing group between a coupler moiety and a photographically useful group, the coupler moiety being joined to the timing group and the timing group being joined to the photographically useful group so that upon reaction of the coupler with oxidized color developing agent the timing group and the photographically useful group are released as a unit from the coupler moiety and thereafter the photographically useful group is released from the timing group by an intramolecular nucleophilic displacement reaction.

Photographic couplers of my invention, in one form, can be represented by the structure:

COUP-TIME-PUG     (I)

where
COUP is a coupler moiety,
TIME is a timing group and
PUG is a photographically useful group.

The coupler moiety can be any moiety which will react with oxidized color developing agent to release the -TIME-PUG group. It includes coupler moieties employed in conventional color-forming couplers which yield colored products on reaction with oxidized color developing agents as well as coupler moieties which yield colorless products on reaction with oxidized color developing agents. Both types of coupler moieties are well known to those skilled in the art and representative patents which describe them are referred to hereinafter.

The coupler moiety can be unballasted or ballasted with an oil-soluble or fat-tail group. It can be monomeric, or it can form part of a dimeric, oligomeric or polymeric coupler, in which case more than one -TIME-PUG group can be contained in the coupler, or it can form part of a bis compound in which the TIME or PUG group forms part of the link between two coupler moieties.

It will be appreciated that, depending upon the particular coupler moiety, the particular color developing agent and the type of processing, the reaction product of the coupler moiety and oxidized color developing agent can be: (1) colored and nondiffusible, in which case it will remain in the location where it is formed; (2) colored and diffusible, in which case it may be removed during processing from the location where it is formed or allowed to migrate to a different location; or (3) colorless and diffusible or non-diffusible, in which case it will not contribute to image density. In cases (2) and (3) the reaction product may be initially colored and/or non-diffusible but converted to colorless and/or diffusible products during the course of processing.

The -TIME-PUG group is joined to the coupler moiety at any of the positions from which groups released from couplers by reaction with oxidized color developing agent can be attached. Preferably, the -TIME-PUG group can be attached to the coupling position of the coupler moiety so that upon reaction of the coupler with oxidized color developing agent the -TIME-PUG group will be displaced. However, the -TIME-PUG group can be in a non-coupling position of the coupler moiety, e.g. as in Bloom U.S. Pat. No. 3,443,940 referred to above, from which position it will be displaced as a result of reaction of the coupler with oxidized color developing agent. In the case where the -TIME-PUG group is in a non-coupling position of the coupler moiety, other groups can be in the coupling position, including conventional coupling-off groups or the same or a different photographically useful group from that contained in the -TIME-PUG group. Alternatively, the coupler moiety can have a -TIME-PUG group in each of the coupling position and a non-coupling position. Accordingly, couplers of this invention can release more than one mole of photographically useful group per mole of coupler. The photographically useful groups can be the same or different and can be released at the same or different times and rates.

The timing group can be any organic group which will serve to connect COUP to PUG and which, after cleavage of the unit -TIME-PUG from COUP, will cleave from PUG by an intramolecular nucleophilic displacement reaction. Such reactions are known in the chemical arts and discussed in, for example, Capon and McManus, *Neighboring Group Participation*, Vol. 1, Plenum Press, New York, 1976. As used herein, the term "intramolecular nucleophilic displacement reaction" is understood to refer to a reaction in which a nucleophilic center of a compound reacts directly, or indirectly through an intervening molecule, at another site on the compound, which is an electrophilic center, to effect displacement of a group or atom attached to the electrophilic center. Such compounds have a nucleophilic group and an electrophilic group spatially related by the configuration of the molecule to promote reactive proximity. Preferably the nucleophilic group and the electrophilic group are located in the compound so that a cyclic organic ring, or a transient cyclic organic ring, can be easily formed by an intramolecular reaction involving the nucleophilic center and the electrophilic center.

A nucleophilic group is understood to be a grouping of atoms one of which is electron rich. This atom is referred to as the nucleophilic center. An electrophilic group is understood to be a grouping of atoms one of which is electron deficient. This atom is referred to as the electrophilic center.

Thus, in photographic couplers of this invention, the timing group contains a nucleophilic group and an electrophilic group which are spatially related with respect to one another so that upon release of -TIME-PUG from the coupler moiety the nucleophilic center and the electrophilic center will react to effect displacement of the photographically useful group from the timing group. In order to assure that the photographically useful group is not released prior to release of -TIME-PUG from the coupler moiety, the nucleophilic center should be prevented from reacting with the electrophilic center until such release and the electrophilic center should be resistant to external attack, e.g. hydrolysis. Premature reaction can be prevented by attaching the coupler moiety to the timing group at the nucleophilic center, so that cleavage of -TIME-PUG from the coupler moiety unblocks the nucleophilic center and permits it to react with the electrophilic center, or by positioning the nucleophilic group and the electrophilic group so that they are prevented from coming into reactive proximity until release. Similarly, the photographically useful group will be attached at a position on the timing group from which it will be displaced upon reaction of the nucleophilic center and the electrophilic center.

Release of the photographically useful group can involve a single reaction once the timing group is cleaved from the coupler moiety or it can involve sequential reactions. For example, two or more sequential intramolecular nucleophilic displacement reactions may be required within the timing group to effect release of the photographically useful group. As another example, the timing group can have two photographically useful groups attached to different locations on the timing group so that upon release of the timing group from the coupler moiety the nucleophilic group first reacts with the electrophilic group joining one of the photographically useful groups to form a transient cyclic ring thereby releasing that photographically useful group and then reacts with the electrophilic group joining the second photographically useful group to release that photographically useful group. As yet another example the intramolecular nucleophilic displacement reaction may release a second coupler which contains another timing group to which the photographically useful group is joined and from which it is released after the second coupler reacts with oxidized color developing agent.

The timing group can contain moieties and substituents which will permit control of one or more of the rate of reaction of COUP with oxidized color developing agent, the rate of diffusion of -TIME-PUG once it is released from COUP and the rate of release of PUG by the intramolecular nucleophilic displacement reaction. The timing group can contain additional substituents, such as additional photographically useful groups, or precursors thereof, which may remain attached to the timing group.

The photographically useful group can be any group that is desirably made available in a photographic element in an imagewise fashion. The photographically useful group can be a photographic dye or a photographic reagent. A photographic reagent is understood to be a moiety which upon release further reacts with components in the element, such as a development inhibitor, a development accelerator, a bleach inhibitor, a bleach accelerator, a coupler (e.g. a competing coupler, a color-forming coupler, a DIR coupler), a developing agent (e.g. a competing developing agent), a silver complexing agent, a fixing agent, a toner, a hardener, a tanning agent, a fogging agent, an antifoggant, a chemical or spectral sensitizer and a desensitizer. Such dyes and photographic reagents generally contain a hetero atom having a negative valence of 2 or 3 from Group VA or VIA of the periodic table, such as oxygen, sulfur, selenium and nitrogen (e.g., nitrogen in a heterocyclic ring). Such an atom can conveniently serve as the point on the dye or photographic reagent at which the TIME group is joined. Preferred hetero atoms in the dye or photographic reagent to which the TIME group is joined are those having a negative valence of 2 from Group VIA of the periodic table, especially sulfur and oxygen.

The photographically useful group can be present in the coupler as a preformed species or it can be present in a blocked form or as a precursor. For example, a preformed development inhibitor may be attached to the timing group or the development inhibiting function may be blocked by being the point of attachment to the timing group. As another example, a preformed dye may be attached to the timing group, a dye which is blocked so as to shift its spectral absorption may be attached to the timing group or a leuco dye may be attached to the timing group.

Preferred compounds according to this invention include a photographic coupler containing a coupler moiety, a photographically useful group containing a hetero atom from Group VA or VIA of the Periodic Table having a negative valence of 2 or 3, and a timing group joining the coupler moiety and the photographically useful group, the timing group comprising a nucleophilic group attached to the coupler moiety at a position from which it is capable of being displaced as a result of reaction of the coupler moiety with oxidized color developing agent, an electrophilic group attached to the photographically useful group and capable of being displaced therefrom by said nucleophilic group after said nucleophilic group is displaced from said coupler moiety, and a linking group spatially relating the nucleophilic group and the electrophilic group to undergo, after cleavage of the bond between the timing group and the coupler moiety, an intramolecular nucleophilic displacement reaction which cleaves the bond between the photographically useful group and the timing group.

It will be appreciated that for an intramolecular reaction to occur between the nucleophilic group and the electrophilic group, the groups should be spatially related within the timing group, after cleavage from the coupler, so that they can react with one another. Preferably, the nucleophilic group and the electrophilic group are spatially related within the timing group so that the intramolecular nucleophilic displacement reaction involves the formation of a three- to seven-membered ring, most preferably a five- or six-membered ring.

It will be further appreciated that for an intramolecular nucleophilic displacement reaction to occur in the aqueous alkaline environment encountered during photographic processing, displacing the photographically useful group from the timing group, the thermodynamics should be such and the groups be so selected that the free energy of ring closure plus the bond energy of the bond formed between the nucleophilic group and the electrophilic group is greater than the bond energy between the electrophilic group and the photographically useful group. Not all possible combinations of nucleophilic group, linking group, electrophilic group and the atom in the photographically useful group to which the electrophilic group is attached will yield a thermodynamic relationship favorable to breaking of the bond between the electrophilic group and the photographically useful group. However, it is within the skill of the art to select appropriate combinations taking the above energy relationships into account. These factors are discussed in more detail in Capon and McManus, *Neighboring Group Participation*, Volume 1, Plenum Press, New York, 1976.

A preferred class of photographic coupler compounds of this invention can be represented by the structure:

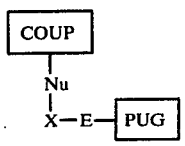
(II)

where:

COUP is a coupler moiety, as described above;

PUG is a photographically useful group, as described above;

Nu is a nucleophilic group attached to a position on COUP from which it will be displaced upon reaction of COUP with oxidized color developing agent;

E is an electrophilic group attached to the hetero atom in PUG and is displacable therefrom by Nu after Nu is displaced from COUP; and X is a linking group for spatially relating Nu and E, upon displacement of Nu from COUP, to undergo an intramolecular nucleophilic displacement reaction with the formation of a three-to seven-membered ring and thereby release PUG.

Representative Nu groups contain electron rich oxygen, sulfur and nitrogen atoms. Representative E groups contain electron deficient carbonyl, thiocarbonyl, phosphinyl and thiophosphinyl moieties. Other useful Nu and E groups will be apparent to those skilled in the art.

In the following listings of representative Nu and E groups, the groups are oriented so that the lefthand bond of Nu is joined to COUP and the righthand bond of Nu is joined to X, while the lefthand bond of E is joined to X and the righthand bond of E is joined to PUG.

Representative Nu groups include:

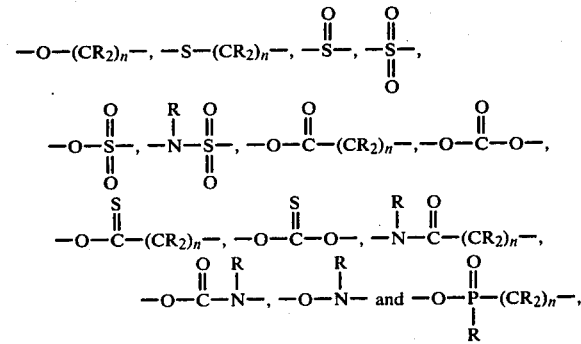

where each R is independently hydrogen, alkyl of 1 to 20 carbon atoms including substituted alkyl such as methyl, ethyl, propyl, hexyl, decyl, pentadecyl, octadecyl, carboxyethyl, hydroxypropyl, sulfonamidobutyl and the like, or aryl of 6 to 20 carbon atoms including substituted aryl such as phenyl, naphthyl, benzyl, tolyl, t-butylphenyl, carboxyphenyl, chlorophenyl, hydroxyphenyl and the like, and n is an integer from 0 to 4 such that the ring formed by Nu, X and E upon nucleophilic attack of Nu upon the electrophilic center in E contains 3 to 7 ring atoms. Preferably R is hydrogen, lower alkyl of 1 to 4 carbon atoms or aryl of 6 to 10 carbon atoms.

Representative E groups include:

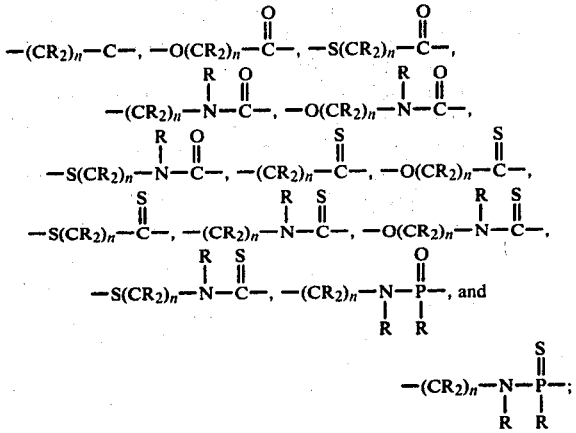

where R and n are defined above.

The linking group represented by X can be an acyclic group such as alkylene (e.g. methylene, ethylene, propylene, etc.) or a cyclic group such as an aromatic group (e.g. phenylene, naphthylene, etc.) or a heterocyclic group (e.g. furan, thiophene, pyridine, quinoline, benzoxazine, etc.). Preferably X is alkylene or arylene. The groups Nu and E are attached to X to provide, upon release of Nu from COUP, favorable spatial relationship for nucleophilic attack of the nucleophilic center in Nu on the electrophilic center in E. When X is a cyclic group, Nu and E can be attached to the same or adjacent rings. Aromatic groups in which Nu and E are attached to adjacent ring positions are particularly preferred X groups.

Particularly preferred couplers of structure II above can be represented by the structure:

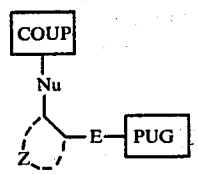
(III)

where:

COUP is a coupler moiety;

Nu is a nucleophilic group attached to the coupling position of COUP, selected from the group consisting of

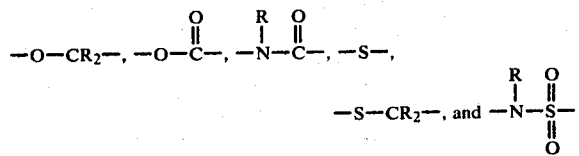

where each R is independently hydrogen, alkyl of 1 to 20 carbon atoms, preferably lower alkyl of 1 to 4 carbon atoms, or aryl of 6 to 20 carbon atoms, preferably aryl of 6 to 10 carbon atoms.

Z represents the atoms necessary to complete a mono- or bicyclic aromatic or heterocyclic ring system containing 5 to 10 ring atoms, preferably containing ring atoms selected from carbon, oxygen, nitrogen and sulfur;

E is an electrophilic group selected from the group consisting of

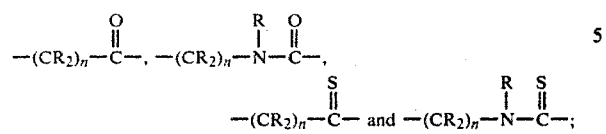

where each R is independently hydrogen, alkyl of 1 to 20 carbon atoms, preferably lower alkyl of 1 to 4 carbon atoms, or aryl of 6 to 20 carbon atoms, preferably aryl of 6 to 10 carbon atoms; and n is an integer of 0 to 4 such that the ring formed upon reaction of the nucleophilic center in Nu with the electrophilic center in E contains 5- to 6-members; and PUG is a photographically useful group containing a hetero atom from Group VA or VIA of the Periodic Table having a negative valence of 2 or 3 through which it is attached to a position in E from which it will be displaced upon nucleophilic attack of Nu at the electrophilic center in E.

In the above structure III the nucleus completed by Z can be unsubstituted or substituted. The substituents can be those which will modify the rate of reaction, diffusion, or displacement, such as halogen (e.g. fluoro, chloro, bromo, iodo), nitro, alkyl of 1 to 20 carbon atoms, acyl (e.g. carboxy, carboxyalkyl, alkoxycarbonyl, alkylcarbonamido, sulfoalkyl, alkylsulfonamido, alkylsulfonyl, etc.), solubilizing groups, ballast groups and the like, or they can be substituents which are separately useful in the photographic element such as a stabilizer, an antifoggant, a dye (e.g., a filter dye, a solubilized masking dye) and the like. For example, solubilizing groups will increase the rate of diffusion; ballast groups will decrease the rate of diffusion; electron withdrawing groups will decrease the rate of displacement of the photographically useful group; and photographically useful groups which remain attached to Z can serve functions such as stabilization, masking and the like.

There follows a listing of patents and publications which describe representative COUP and PUG groups useful in the invention. Also listed are structures of preferred COUP, TIME and PUG groups. In these structures the unsatisfied bonds in each of COUP and PUG show the point of attachment to TIME, the vertical unsatisfied bond in TIME shows the point of attachment of COUP and the horizontal unsatisfied bond in TIME shows the point of attachment to PUG.

I. COUP's

A. Couplers which form cyan dyes upon reaction with oxidized color developing agents are described in such representative patents and publications as: U.S. Pat. Nos. 2,772,162, 2,895,826, 3,002,836, 3,034,892, 2,474,293, 2,423,730, 2,367,531, 3,041,236 and "Farbkuppler-eine Literaturübersicht," published in Agfa Mitteilungen, Band II, pp. 156-175 (1961).

Preferably such couplers are phenols and naphthols which form cyan dyes on reaction with oxidized color developing agent and have the -TIME-PUG group attached to the coupling position, i.e. the carbon atom in the 4-position. Structures of preferred such coupler moieties are:

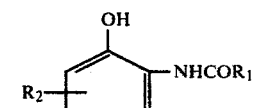

IA-1

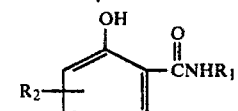

IA-2

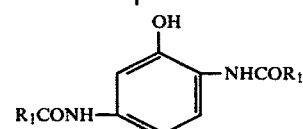

IA-3

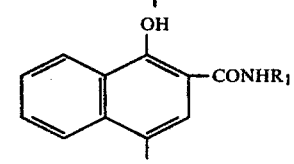

IA-4 where $R_1$ represents a ballast group, and $R_2$ represents one or more halogen (e.g. chloro, fluoro), lower alkyl (e.g. methyl, ethyl, butyl) or lower alkoxy (e.g. methoxy, ethoxy, butoxy) groups.

B. Couplers which form magenta dyes upon reaction with oxidized color developing agent are described in such representative patents and publications as: U.S. Pat. Nos. 2,600,788, 2,369,489, 2,343,703, 2,311,082, 3,152,896, 3,519,429, 3,062,653, 2,908,573 and "Farbkuppler-eine Literatürubersicht," published in Agfa Mitteilungen, Band II, pp. 126-156 (1961).

Preferably such couplers are pyrazolones and pyrazolotriazoles which form magenta dyes upon reaction with oxidized color developing agents and have the -TIME-PUG group attached to the coupling position, i.e. the carbon atom in the 4-position. Structures of preferred such coupler moieties are:

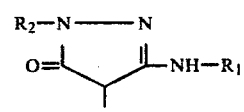

IB-1

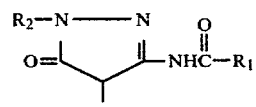

IB-2

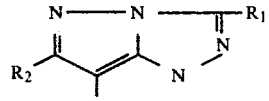

IB-3 where $R_1$ is as defined above and $R_2$ is as defined above or is phenyl or substituted phenyl (e.g. 2,4,6-trihalophenyl).

C. Couplers which form yellow dyes upon reaction with oxidized and color developing agent are described in such representative patents and publications as: U.S. Pat. Nos. 2,875,057, 2,407,210, 3,265,506, 2,298,443, 3,048,194, 3,447,928 and "Farbkuppler-eine Literatürü bersicht," published in Agfa Mitteilungen, Band II, pp. 112-126 (1961).

Preferably such yellow-dye forming couplers are acylacetamides, such as benzoylacetanilides and pivalylacetanilides, and have the -TIME-PUG group attached to the coupling position, i.e. the active methylene carbon atom.

Structures of preferred such coupler moieties are:

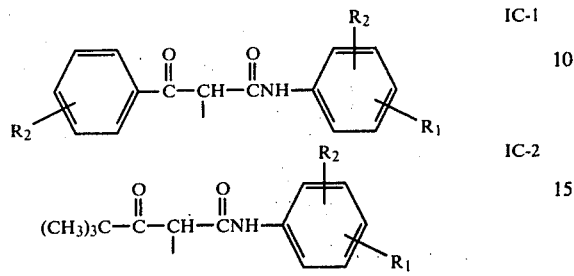

IC-1

IC-2 where $R_1$ is as defined above and $R_2$ is hydrogen or one or more halogen, lower alkyl (e.g. methyl, ethyl) or ballast (e.g. alkoxy of 16 to 20 carbon atoms) groups.

D. Couplers which form colorless products upon reaction with oxidized color developing agent are described in such representative patents as: U.K. Pat. No. 861,138; U.S. Pat. Nos. 3,632,345, 3,928,041, 3,958,993 and 3,961,959. Preferably such couplers are cyclic carbonyl containing compounds which form colorless products on reaction with oxidized color developing agent and have the -TIME-PUG group attached to the carbon atom in the α-position with respect to the carbonyl group.

Structures of preferred such coupler moieties are:

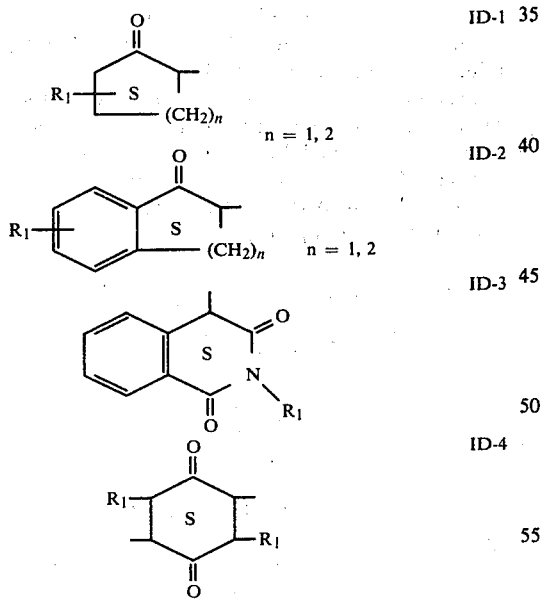

ID-1

ID-2

ID-3

ID-4 where $R_1$ is as defined above.

E. Couplers which form black dyes upon reaction with oxidized color developing agent are described in such representative patents and patent applications as U.S. Pat. Nos. 1,939,231, 2,181,944, 2,333,106, U.S. Patent Application Ser. No. 806,244 filed Jan. 13, 1977, German OLS No. 2,644,194 and German OLS No. 2,650,764.

Preferably such couplers are resorcinols or m-aminophenols which form black or neutral products on reaction with oxidized color developing agent and have the -TIME-PUG group para to a hydroxy group.

Structures of preferred such coupler moieties are:

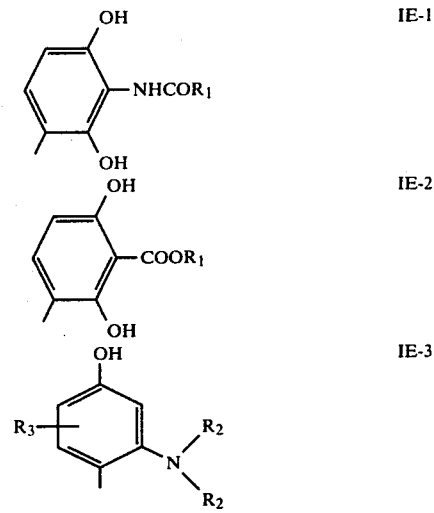

IE-1

IE-2

IE-3 where $R_1$ is alkyl of 3 to 20 carbon atoms, phenyl or phenyl substituted with hydroxy, halo, amino, alkyl of 1 to 20 carbon atoms or alkoxy of 1 to 20 carbon atoms; each $R_2$ is independently hydrogen, halogen, alkyl of 1 to 20 carbon atoms, alkenyl of 1 to 20 carbon atoms, or aryl of 6 to 20 carbon atoms; and $R_3$ is one or more halogen, alkyl of 1 to 20 carbon atoms, alkoxy of 1 to 20 carbon atoms or other monovalent organic groups.

II. TIME's

A. Acrylic TIME groups:

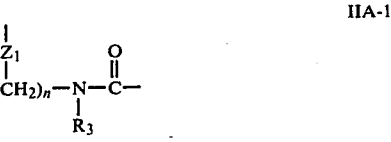

IIA-1 where n is 1–4, preferably 2 or 3, $Z_1$ is

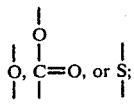

and $R_3$ is hydrogen, alkyl of 1 to 20 carbon atoms, preferably lower alkyl of 1 to 4 carbon atoms, or aryl of 6 to 20 carbon atoms, preferably aryl of 6 to 10 carbon atoms.

B. Aromatic TIME groups:

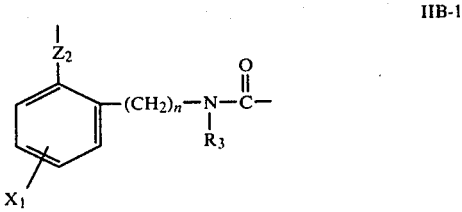

IIB-1

-continued

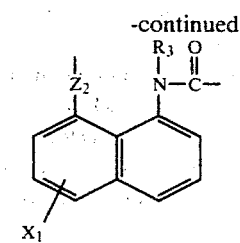
IIB-2 where n is 0 or 1; $Z_2$ is

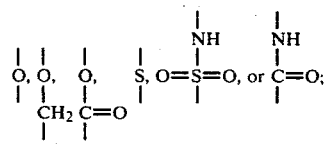

$R_3$ is as defined above; and $X_1$ is hydrogen, cyano, fluoro, chloro, bromo, iodo, nitro, alkyl of 1 to 20 carbon atoms, a dye, —$OR_4$, —$COOR_4$, —$CONHR_4$, —$NHCOR_4$, —$NHSO_2R_4$, —$SO_2NHR_4$ of $SO_2R_4$ where $R_4$ is hydrogen, alkyl of 1 to 20 carbon atoms, preferably alkyl of 1 to 4 carbon atoms, or aryl of 6 to 20 carbon atoms, preferably, aryl of 6 to 10 carbon atoms.

C. Heterocyclic TIME groups:

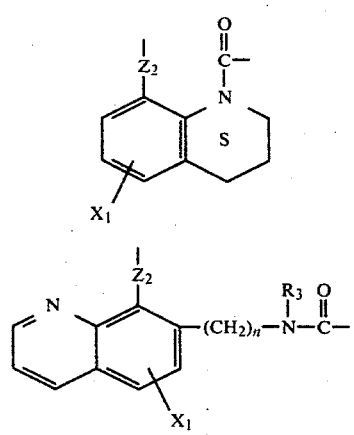
IIC-1

IIC-2 where n is 0 or 1, $Z_2$, $X_1$ and $R_3$ are as defined above.

D. Bis TIME groups:

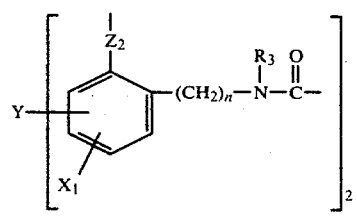
IID-1 where Y is a linking group, such as

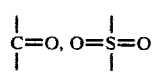

or —$NHSO_2CH_2SO_2NH$—; n is 0 or 1 and $X_1$, $Z_2$ and $R_3$ are as defined above.

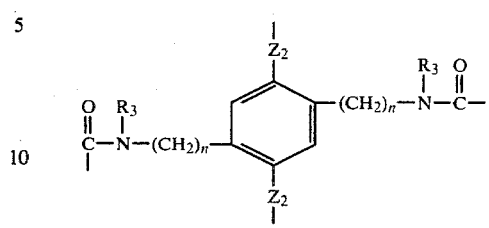
IID-2 where n is 0 or 1 and $Z_2$, and $R_3$ are as defined above.

III. PUG's

A. PUG's which form development inhibitors upon release from TIME are described in such representative patents as U.S. Pat. Nos. 3,227,554; 3,384,657; 3,615,506; 3,617,291, 3,733,201 and U.K. Pat. No. 1,450,479. Preferred development inhibitors are iodide and heterocyclic compounds such as mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzotriazoles and benzodiazoles. Structures of preferred development inhibitor moieties are:

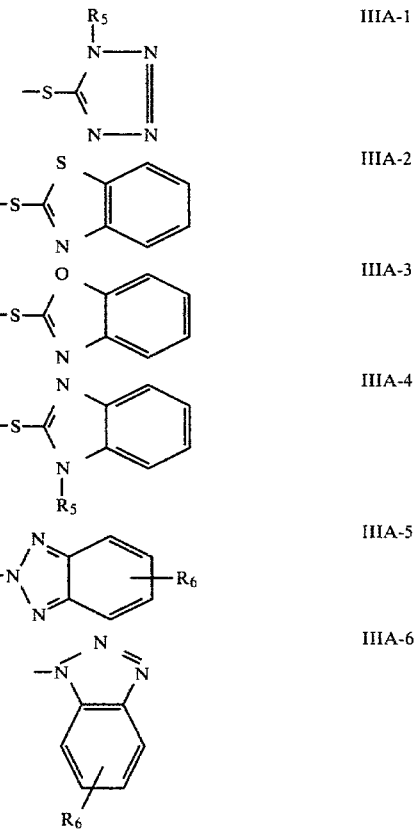

where $R_5$ is hydrogen, alkyl of 1 to 8 carbon atoms (e.g. methyl, ethyl, butyl), phenyl or substituted phenyl and $R_6$ is hydrogen or one or more halogen (e.g. chloro, fluoro, bromo), or lower alkyl of 1 to 4 carbon atoms or nitro groups.

B. PUG's which are, or form, dyes upon release from -TIME-:

Suitable dyes and dye precursors include azo, azomethine, azopyrazolone, indoaniline, indophenol, anthraquinone, triarylmethane, alizarin, nitro, quinoline, indigoid and phthalocyanine dyes or precursors of such dyes such as leuco dyes, tetrazolium salts or shifted dyes. These dyes can be metal complexed or metal complexable. Representative patents describing such dyes are U.S. Pat. Nos. 3,880,658; 3,931,144; 3,932,380; 3,932,381 and 3,942,987. Preferred dyes and dye precursors are azo, azomethine and indoaniline dyes and dye precursors. Structures of some preferred dyes and dye precursors are:

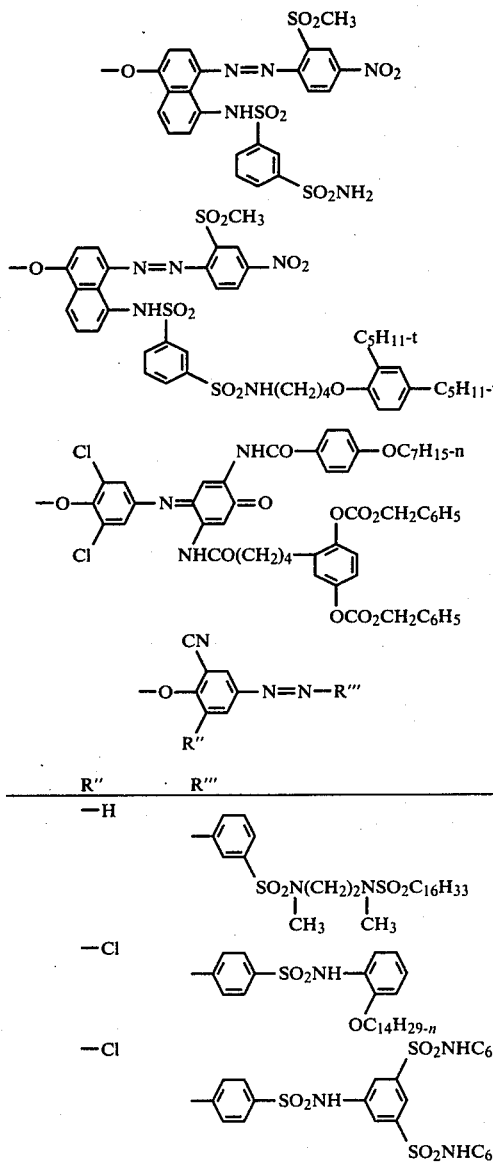

C. PUG's which are couplers:

Couplers released from -TIME- can be non-diffusible color-forming couplers, non-color forming couplers or diffusible competing couplers. Representative patents and publications and preferred structures for the first two categories are shown above in IA through IE. Representative patents and publications describing competing couplers are: "On the Chemistry of White Couplers," by W. Püschel, Agfa-Gevaert AG Mitteilungen ans der Forschungs-Laboratorium der Agfa-Gevaert AG, Springer Verlag, 1954, pp. 352–367; U.S. Pat. Nos. 2,998,314, 2,808,329, 2,689,793; 2,742,832; German Pat. No. 1,168,769 and British Pat. No. 907,274. Structures of preferred competing couplers are:

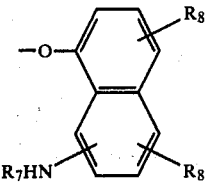

where $R_7$ is hydrogen or alkylcarbonyl (e.g. acetyl) and $R_8$ is hydrogen or a solubilizing group (e.g. sulfo, aminosulfonyl, carboxy, etc.).

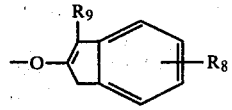

where $R_8$ is as defined above and $R_9$ is halogen, aryloxy, arylthio, or a development inhibitor, such as a mercaptotetrazole (e.g. phenylmercaptetrazole or ethyl mercaptotetrazole.)

D. PUG's which form developing agents:

Developing agents released from -TIME- can be color developing agents, black-and-white developing agents or cross-oxidizing developing agents. They include aminophenols, phenylene diamines, hydroquinones and pyrazolidones. Representative patents are: U.S. Pat. Nos. 2,193,015, 2,108,243, 2,592,364, 3,656,950, 3,658,525, 2,751,297, 2,289,367, 2,772,282, 2,743,279, 2,753,265 and 2,304,953.

Structures of preferred developing agents are:

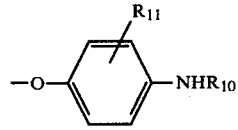

where $R_{10}$ is hydrogen or lower alkyl of 1 to 4 carbon atoms and $R_{11}$ is hydrogen or one or more halogen (e.g. chloro, bromo) or lower alkyl (e.g. methyl, ethyl, butyl) groups.

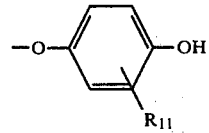

where $R_{11}$ is as defined above.

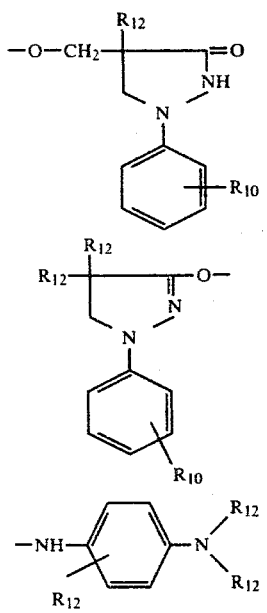

IIID-3

IIID-4

IIID-5 where $R_{10}$ is as defined above and $R_{12}$ is hydrogen, lower alkyl of 1 to 4 carbon atoms (e.g. methyl, ethyl) lower hydroxyalkyl of 1 to 4 carbon atoms (e.g. hydroxymethyl, hydroxyethyl) or lower sulfoalkyl.

E. PUG's which are bleach inhibitors:

Representative patents are U.S. Pat. Nos. 3,705,801, 3,715,208 and German OLS No. 2,405,279. Structures of preferred bleach inhibitors are:

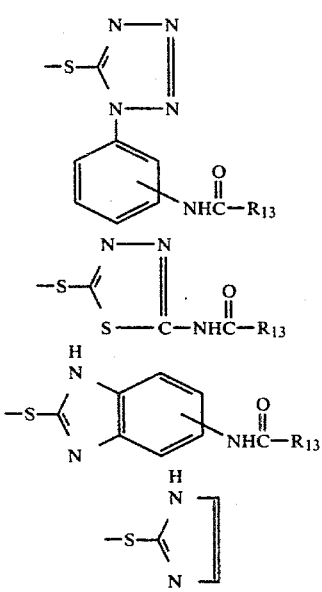

IIIE-1

IIIE-2

IIIE-3

IIIE-4 where $R_{13}$ is an alkyl group of 6 to 20 carbon atoms.

Typically, the couplers of this invention are prepared by attaching to the appropriate coupler moiety, or a derivative of the coupler moiety, the linking group through the nucleophilic group. The linking group will have, in the appropriate spatial relationship to the nucleophilic group, a derivative of the electrophilic group, or another suitable functional group, which will form the electrophilic group when the photographically useful group is attached. This is then reacted with an appropriate derivative of the photographically useful group to form the desired coupler. Known reactions are employed to perform these steps. The working examples show the way in which these steps can be performed using specific reactants and reactions.

The photographic couplers of this invention can be incorporated in photographic elements or in photographic processing solutions, such as developer solutions, so that upon development of an exposed photographic element they will be in reactive association with oxidized color developing agent. Coupler compounds incorporated in photographic processing solutions should be of such molecular size and configuration that they will diffuse through photographic layers with the processing solution. When incorporated in a photographic element, as a general rule, the coupler compounds should be non-diffusible, i.e. they should be of such molecular size and configuration that they will not significantly diffuse or wander from the layer in which they are coated.

Photographic elements of this invention can be processed by conventional techniques in which color forming couplers and color developing agents are incorporated in separate processing solutions or compositions or in the element. The elements can be processed by redox amplification techniques in which developed or latent image silver acts as a catalyst for oxidation of the color developing agent by an oxidizing agent such as a transition metal complex (e.g. cobalt hexamine or a peroxide (e.g. hydrogen peroxide). Amplification processing is described, for example, in U.S. Pat. Nos. 3,674,490; 3,822,129; 3,834,907; 3,841,873; 3,847,619; 3,862,842; 3,902,905 and 3,923,511.

Photographic elements in which the photographic couplers of this invention are incorporated can be a simple element comprising a support and a single silver halide emulsion layer or they can be multilayer, multicolor elements. The coupler compounds of this invention can be incorporated in the silver halide emulsion layer or in another layer, such as an adjacent layer, where they will come into reactive association with oxidized color developing agent which has developed silver halide in the emulsion layer. The silver halide emulsion layer can contain, or have associated with it, other photographic coupler compounds, such as color forming couplers, colored masking couplers, etc. These other photographic coupler compounds can form dyes of the same or different color and hue as the photographic coupler compounds of this invention. Additionally, the silver halide emulsion layer can contain addenda conventionally contained in such layers.

A typical multilayer, multicolor photographic element according to this invention can comprise a support having thereon a red-sensitive silver halide emulsion unit having associated therewith a cyan dye image providing material, a green-sensitive silver halide emulsion unit having associated therewith a magenta dye image providing material and a blue-sensitive silver halide emulsion unit having associated therewith a yellow dye image-providing material, at least one of the silver halide emulsion units having associated therewith a photographic coupler of the invention. Each silver halide emulsion unit can be composed of one or more layers and the various units and layers can be arranged in different locations with respect to one another. Typical arrangements are described in U.S. Pat. Nos. 3,227,554; 3,620,747; 3,843,369; U.S. Application Ser. No. 758,251 filed Jan. 10, 1977 and U.K. Pat. No. 923,045. The coupler compounds of this invention can be incorporated in or associated with one or more layers or units of the element. If -TIME-PUG or PUG is a diffusible moiety, the layer(s) and unit(s) affected by PUG can be controlled by incorporating in appropriate locations in the element scavenger layer(s) which will confine the action of PUG to the desired layer(s) or unit(s).

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids can be used in accordance with usual practice.

The support can be any suitable support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylene-butene copolymers and the like.

Further details regarding silver halide emulsions and elements, and addenda incorporated therein can be found in *Research Disclosure*, December 1971, Item 9232, Paragraphs I through XVIII. *Research Disclosure* is published by Industrial Opportunities Ltd., Homewell, Havant, Hampshire, PO9 1EF, United Kingdom.

The novel photographic couplers of my invention can be used in photographic elements in the same way as photographic couplers which release photographically useful groups have previously been used in photographic elements. However, because of the improved ability to control the release of the photographically useful group, my couplers permit enhanced effects or more selective effects than heretofore possible. In addition, my couplers can be employed in applications where conventional couplers have previously been employed and a separate component was employed to provide a photographically useful group.

Depending upon the nature of the particular photographically useful group, my couplers can be incorporated in a photographic element for different purposes and in different locations and these elements can contain various other components. Reference will be made to exemplary ways in which preferred photographically useful groups can be incorporated.

When the photographically useful group released from the coupler is a development inhibitor, it can be employed in a photographic element as described, for example, in U.S. Pat. Nos. 3,227,554; 3,620,747; 3,703,375 and U.S. Patent Application Ser. No. 758,251 filed Jan. 10, 1977. Other patents and applications describing ways in which couplers which release development inhibitors can be employed are U.K. Pat. No. 1,460,991; U.S. Pat. No. 3,892,572 and German OLS No. 2,516,982. Couplers of this invention which release a development inhibitor can be contained in, or in reactive association with, one or more of the silver halide emulsion units in a color photographic element. If the silver halide emulsion unit is composed of more than one layer, one or more of such layers can contain the coupler of this invention. The layers can contain other photographic couplers conventionally used in the art. The couplers of this invention can form dyes of the same color as the color forming coupler(s) in the layer or unit, it can form a dye of a different color, or it can result in a colorless or neutral reaction product. The range of operation of the development inhibitor between layers when released from the coupler of this invention can be controlled by the use of scavenger layers, such as a layer of a fine grain silver halide emulsion. Scavenger layers can be in various locations in an element containing couplers of this invention. They can be located between layers, between the layers and the support, or over all of the layers.

Couplers of this invention which release development inhibitors can enhance the effects heretofore obtained with DIR couplers since they can release a development inhibitor at a distance from the point at which oxidized color developing agent reacted with the coupler, in which case they can provide enhanced interlayer interimage effects and enhanced intralayer chemical adjacency effects. Thus, the couplers of this invention can be employed to provide a degree of control over the effects obtainable from DIR couplers which heretofore could not be attained.

Photographic couplers of this invention which release bleach inhibitors can be employed in the ways described in U.S. Pat. No. 3,705,801, to inhibit the bleaching of silver in selected areas of a photographic element.

Photographic couplers of this invention which release a dye or dye precursor can be used in processes where the dye is allowed to diffuse to an integral or separate receiving layer to form a desired image as described for example in U.S. Pat. Nos. 3,227,551; 3,443,940 and 3,751,406. Alternatively, the dye can be retained in the location where it is released to augment the density of the dye formed from the coupler from which it is released or to modify or correct the hue of that dye or another dye. In another embodiment, the dye can be completely removed from the element and the dye which was not released from the coupler can be retained in the element as a color correcting mask.

Couplers of this invention in which the photographically useful group is a coupler can be employed to release another coupler. If the released coupler is a dye-forming coupler it can react with oxidized developing agent in the same or an adjacent layer to form a dye of the same or a different color or hue as that obtained from the primary coupler. If the released coupler is a competing coupler it can react with oxidized color developing agent in the same or an adjacent layer to reduce dye density.

Photographic couplers of this invention in which the photographically useful group is a developing agent can be used to release a developing agent which will compete with the color forming developing agent, and thus reduce dye density. Alternatively, they can provide, in an imagewise manner, a developing agent which because of such considerations as activity would not desirably be introduced into the element in a uniform fashion.

The following examples further illustrate this invention.

Preparative Example 1

Preparation of a Cyan Coupler Which Releases A Development Inhibitor:

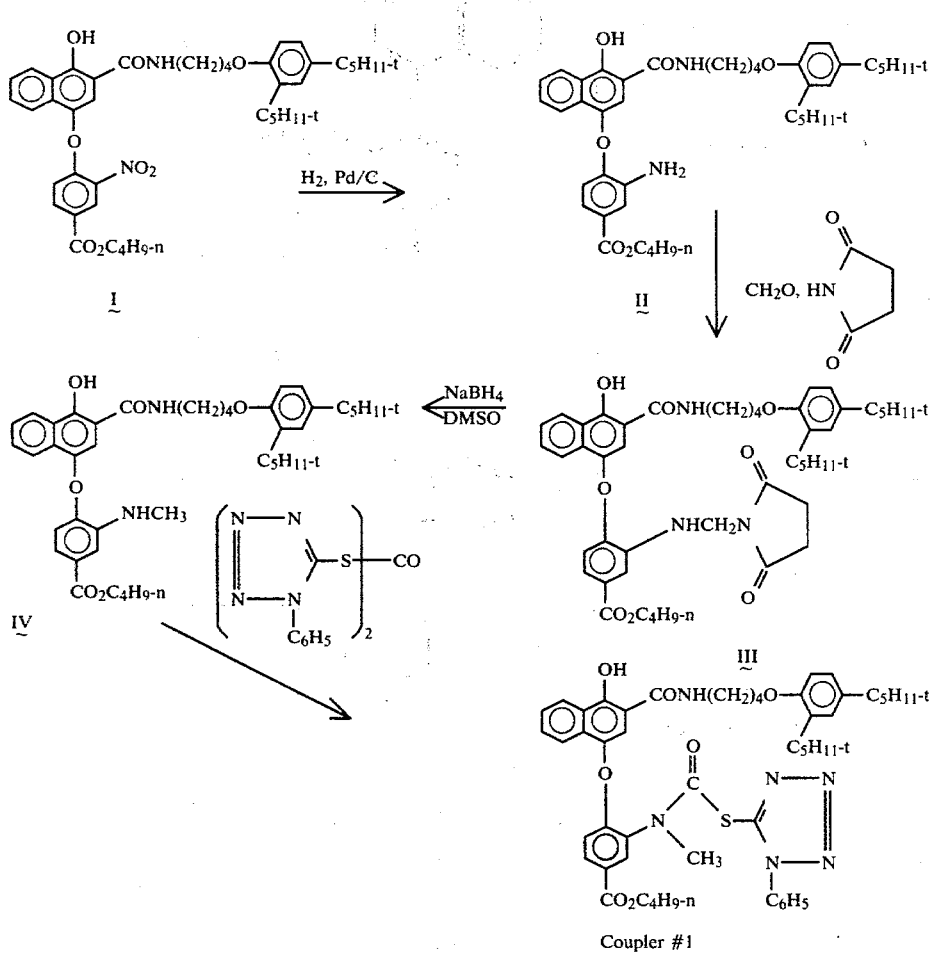

Coupler #1

Preparation of Compound II

In a 1-liter stainless steel Parr hydrogenation vessel was placed 100 g (0.14 mol) of compound I, 1.0 g of 10% Pd/C catalyst, and 500 ml ethyl acetate. The mixture was reduced under 40 p.s.i. of hydrogen at ambient temperature. After the theoretical uptake of hydrogen, the catalyst was removed and the solvent evaporated in vacuo. The crude product was recrystallized from acetonitrile to give 67 g (70%) of white crystalline solid; m.p. 174°–175° C.

Preparation of Compound III

A 500 ml 3-neck round bottom flask was charged with 50 g (0.073 mol) of compound II, 14.5 g (0.15 mol) of succinimide, 11.9 ml (0.15 mol) of formalin, and 250 ml ethanol. The reaction mixture was heated on a steam bath for 30 hours. After cooling, the mixture was poured into 1200 ml water and 60 ml ethyl acetate, with thorough stirring. The organic phase was separated, dried over magnesium sulfate, and the solvent evaporated in vacuo. The crude residue was taken up in a minimum amount of benzene and chromatographically separated with a silica-gel column using benzene and ethyl acetate as eluants. The fractions containing the product were combined and the solvent evaporated in vacuo. The solid residue was recrystallized from hexane giving 30.4 g (53%) of pure colorless crystalline product; m.p. 102°–105° C.

Preparation of Compound IV

To a stirred solution of 30.4 g (0.04 mol) of compound III in 250 ml dimethyl sulfoxide was added portionwise 1.8 g (0.05 mol) of sodium borohydride, maintaining the temperature below 40° C. After stirring for an additional 30 minutes, the mixture was poured into water and extracted with ethyl acetate. The organic extracts were combined, washed with brine, dried over magnesium sulfate and the solvent evaporated in vacuo. The residue was taken up in a minimum amount of benzene and eluted with benzene-ethyl acetate mixtures through a silica-gel column. The fractions containing the product were combined and evaporated in vacuo. The residue was recrystallized from hexane giving 15.5 g (60%) of white crystalline material; m.p. 144°–146° C.

Preparation of Coupler #1

To a stirred solution of 7.0 g (0.01 mol) of compound IV in 35 ml of tetrahydrofuran (THF) was added dropwise under a nitrogen atmosphere 12 ml (1.0 M solution in THF) of S,S'-carbonyl-di-1-phenyl-5-mercaptotetrazole. The reaction mixture was stirred for 2 hours, poured into ice-water and extracted with ethyl acetate. The extracts were dried over magnesium sulfate and evaporated in vacuo. The pale yellow residue was recrystallized from ethyl acetate-ligroine yielding 5.0 g (56%) of pure colorless long needles; m.p. 114°–117° C.

Using similar reaction procedures the following couplers were prepared:

Coupler #2

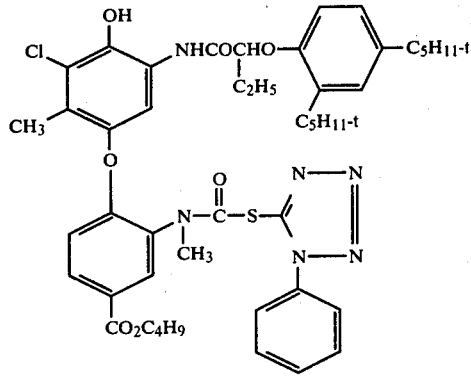

Coupler #3

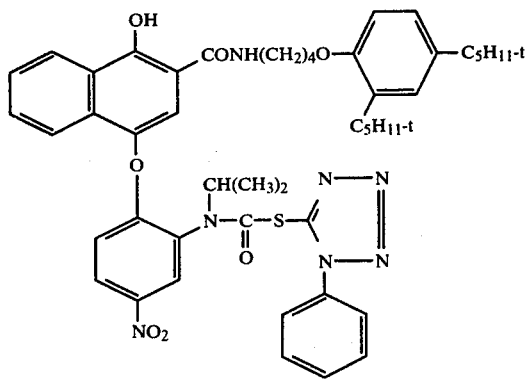

Coupler #4

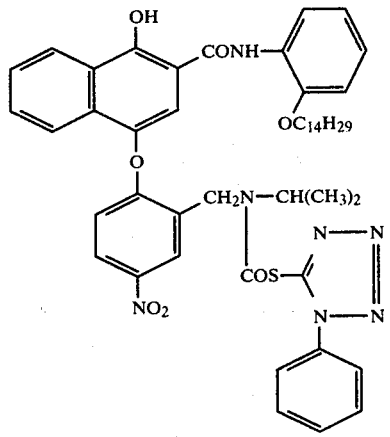

Coupler #5

| Coupler No. | Z | X | n | R |
|---|---|---|---|---|
| 6 | O | NO$_2$ | 0 | —⬡ |
| 7 | S | NO$_2$ | 1 | —⬡ |
| 8 | O | NO$_2$ | 1 | —⬡—OC$_2$H$_5$ |
| 9 | O | NO$_2$ | 1 | —⬡-NHCOCH$_3$ |
| 10 | O | NO$_2$ | 1 | —⬡-NHCOC$_3$H$_7$ |
| 11 | O | NHSO$_2$C$_4$H$_9$ | 0 | —⬡ |
| 12 | O | NHSO$_2$C$_8$H$_{17}$ | 1 | —⬡ |
| 13 | S | H | 0 | —⬡ |

-continued

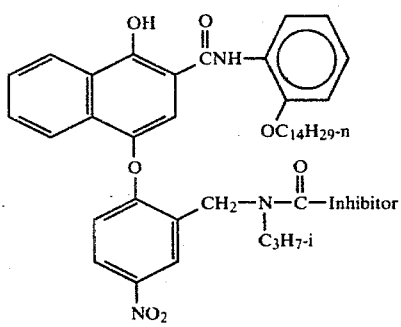

| Coupler No. | X | R |
|---|---|---|
| 14 | —NO$_2$ | —C$_6$H$_4$—CO$_2$CH$_3$ |
| 15 | —NO$_2$ | —C$_6$H$_4$—COOH |
| 16 | —NO$_2$ | —C$_6$H$_4$—OH |
| 17 | —NHCO(CH$_2$)$_3$COOH | —CH(CH$_3$)$_2$ |
| 18 | —NHSO$_2$—C$_6$H$_4$—COOH | —CH(CH$_3$)$_2$ |

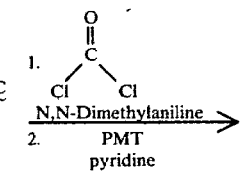

| Coupler No. | Inhibitor |
|---|---|
| 19 | Ethylmercaptotetrazole |
| 20 | n-Butylmercaptotetrazole |
| 21 | Cyclohexylmercaptotetrazole |
| 22 | N-Heptylmercaptotetrazole |
| 23 | 5,6-Dichlorobenzotriazole |

PREPARATIVE EXAMPLE 2

Preparation of a Cyan Coupler Which Releases a Development Inhibitor:

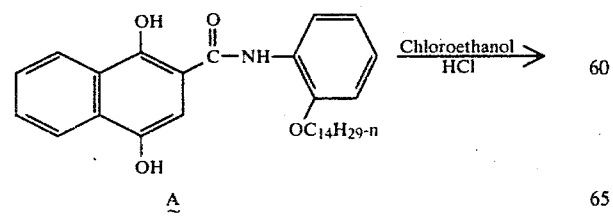

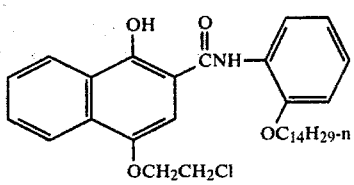

Hydrogen chloride was bubbled through a solution of 20 g (42.2 mmol) of Compound A in 100 ml of chloroethanol, which was heated to 80°–110° C., for 3 hours. After cooling overnight, a crystalline solid formed. The solid product was collected and recrystallized from ethanol-acetone to give 15.5 g of Compound B, m.p. 94.5°–95° C.

Step 2

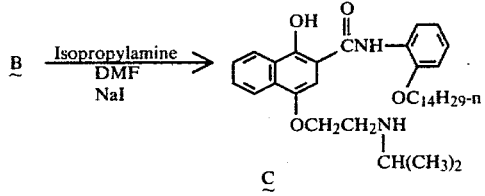

A mixture of 10 g (18 mmol) of Compound B, 25 ml isopropylamine, 25 ml dry N,N-dimethylformamide, and 0.3 g sodium iodide was refluxed for 24 hours. After cooling, the reaction mixture was poured into water and extracted with ether. The organic extracts were washed with water and saturated sodium chloride solution, dried over magnesium sulfate and concentrated to give an orange gummy solid. Recrystallization from hexane yielded 5.7 g of Compound C, m.p. 69.5°–70° C.

Step 3

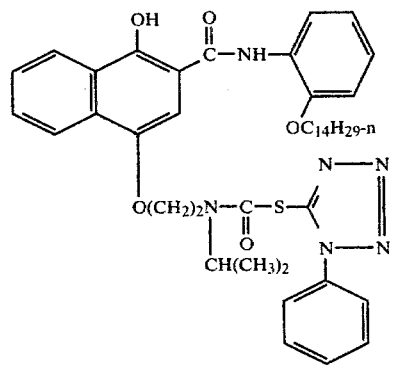

Coupler #24

To a stirred solution of 141 ml phosgene (0.66 M in toluene) was added dropwise, over a 15 minute period, a solution of 5.35 g (9.29 mmol) of Compound C and 1.12 g (9.29 mmol) of N,N-dimethylaniline in 60 ml of toluene. After stirring for two hours, the reaction mixture was filtered and concentrated. To this was added 40 ml pyridine and 1.65 g (9.29 mmol) of 1-phenyl-5-mercaptotetrazole. After stirring for 15 hours, the mixture was poured into 5% hydrochloric acid solution and extracted with ether. The ether extracts were washed with 5% hydrochloric acid solution, saturated sodium bicarbonate solution, and saturated sodium chloride solution, dried over magnesium sulfate, concentrated, and treated with ethanol-water to give a light tan solid. Recrystallization from hexane-ethyl acetate, elution with hexane-ethyl acetate from a silica gel column, and another recrystallization from hexane-ethyl acetate yielded 1.3 g of Coupler #24, m.p. 96.5°–97.5° C.

Using similar reaction procedures the following couplers were prepared:

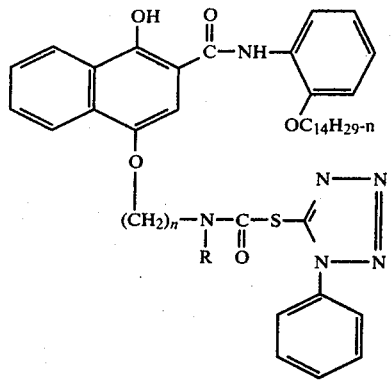

| Coupler No. | n | R |
|---|---|---|
| 25 | 3 | i-propyl |
| 26 | 2 | cyclohexyl |
| 27 | 2 | cyclooctyl |

PREPARATIVE EXAMPLE 3

Preparation of a Yellow Coupler Which Releases A Development Inhibitor:

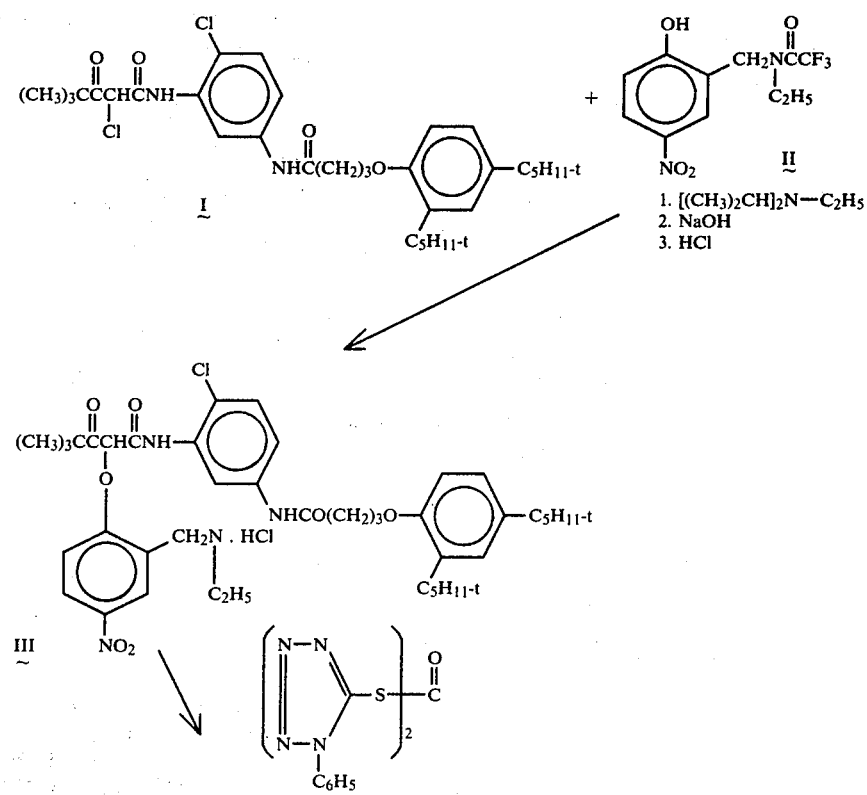

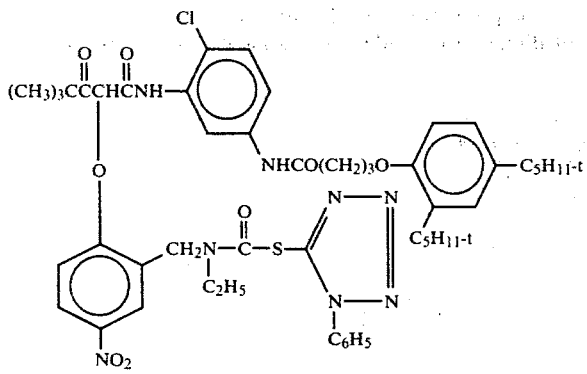

Coupler #28

Preparation of Compound III

To a solution of 16.0 g (0.055 mol) of 2-N-ethyl trifluoroacetamido-methyl-4-nitrophenol in 250 ml acetonitrile was added with stirring 7.10 g (0.055 mol) of di-isopropyl ethylamine and 30.4 g (0.050 mol) of α-pivalyl-α-chloro-[2-chloro-5-γ(2,4-di-tert-amylphenoxy)butylamido]acetanilide. The mixture was heated on a steam bath for 1½ hours. The solvent was evaporated in vacuo yielding a yellow oil. The oil was taken up in 200 ml of methanol and reacted with a solution of 20 g (0.5 mol) of sodium hydroxide in 50 ml of water. After stirring for 1 hour, the dark red solution was poured into 800 ml of ice water and 200 ml of concentrated hydrochloric acid. The solid was collected, triturated with ethyl acetate and then washed with ether. Yield of the desired amine hydrochloride salt was 35.8 g (89%); m.p. 184°–186° C.

Preparation of Coupler #28

To a mixture of 18.5 g (0.023 mol) of compound III suspended in 300 ml of ethyl acetate was added with vigorous stirring 150 ml of a saturated sodium bi-carbonate solution. When all the solid had dissolved, the organic phase was separated, dried over magnesium sulfate and filtered. To the filtrate was added with stirring 8.8 g (0.023 mol) of S,S'-carbonyldi-1-phenyl-5-mercaptotetrazole prepared by bubbling phosgene into a benzene solution of 1-phenyl-5-mercaptotetrazole. The reaction mixture was stirred for 30 minutes after which the solvent was evaporated in vacuo. The residue was chromatographically separated with a silica-gel column using hexaneethyl acetate mixtures as eluants. The fractions containing the pure product were combined and evaporated in vacuo to give 10 g (45%) of Coupler #28; m.p. 77°–80° C.

Using a similar reaction procedure, Coupler #29 was prepared.

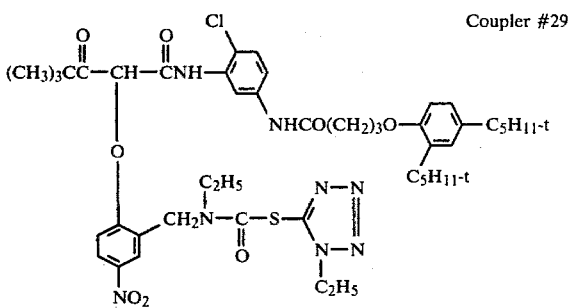

Coupler #29

Coupler #30 was prepared by the catalytic reduction of Coupler #28 using 10% Pd/C and reacting the resulting amine with acetic anhydride: m.p. 115°–117° C.

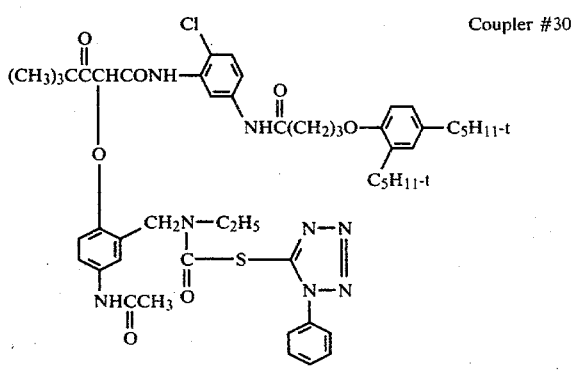

Coupler #30

PREPARATIVE EXAMPLE 4

Preparation of a Cyan Coupler Which Releases a Cyan Dye:

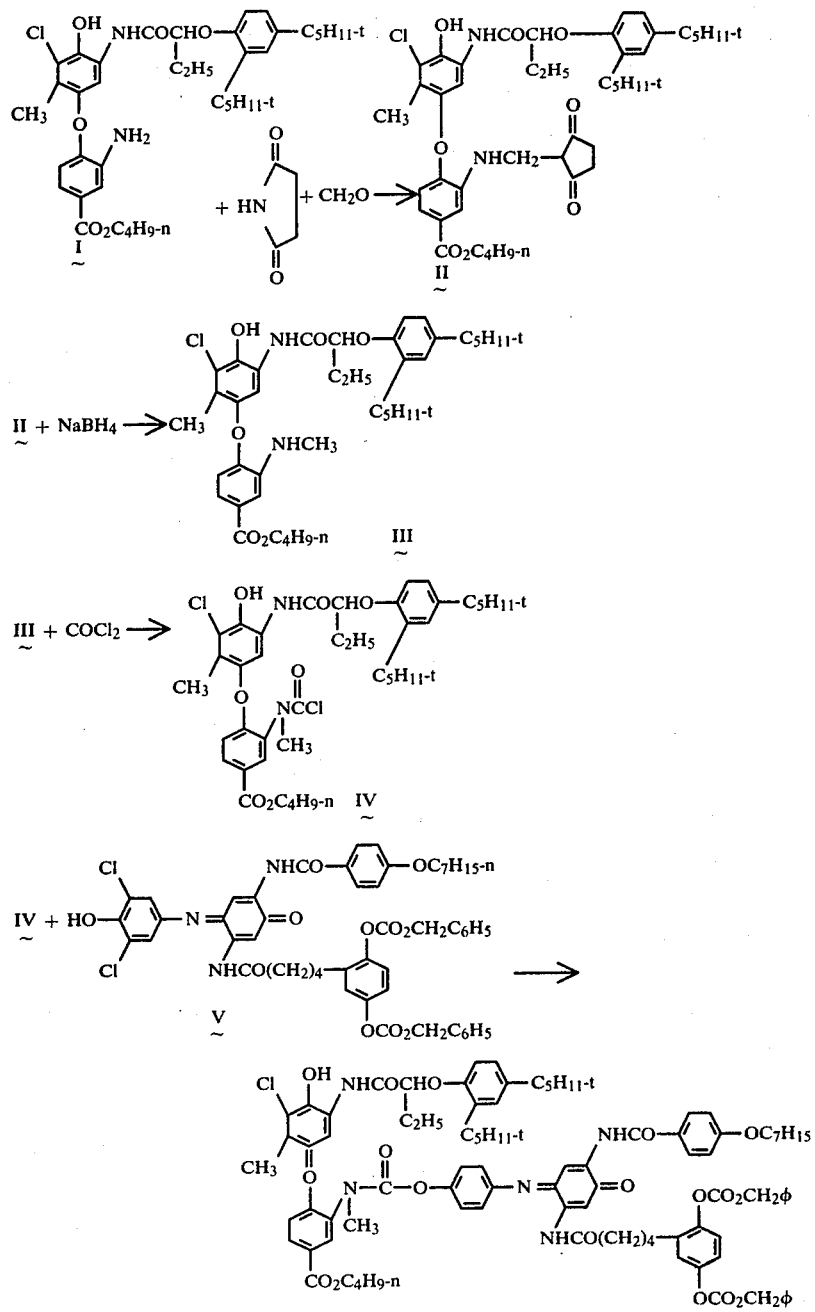

Coupler #31

Preparation of Compound III

To a mixture of 26.7 g of compound I, 5.3 g of succinimide, 10 drops of trifluoroacetic acid and 240 ml of di-n-butyl ether heated at 100°–110° C., was added with stirring 1.7 g of paraformaldehyde. After heating for 1.5 hours, the mixture was cooled and the solvent was removed on a rotary evaporator. The residue was taken up in dichloromethane and passed through a silica gel column to give 20 g of the succinimidomethyl derivative II.

The product obtained above was dissolved in 100 ml of dimethylsulfoxide and warmed to 40° C. With stirring, 4.0 g of sodium borohydride was added in portions. It was then heated on a steam bath for 1.5 hours. The mixture was cooled and poured cautiously with stirring into 1.2 liters ice-water and 40 ml acetic acid. The white solid was collected, dissolved in 600 ml of dichloromethane, dried over MgSO₄, filtered and the filtrate passed through a short silica gel column using dichloromethane as the eluant. The solvent was removed under reduced pressure, and the residue was recrystallized from acetonitrile to give 10.7 g of pure compound III.

Preparation of Coupler #31

To a solution of 4.1 g of compound III in 60 ml of dried benzene was added with stirring 50 ml of 12% solution of phosgene in benzene. The mixture was stirred at room temperature for 3 hours. The solvent was removed under reduced pressure. The carbamoyl chloride derivative IV thus obtained was dissolved in 20 ml tetrahydrofuran and added to a solution of 5.9 g of indophenol dye V in 50 ml of dried pyridine. The reaction mixture was stirred at room temperature for one hour and then heated on a steam bath overnight. The solvent was removed under reduced pressure giving an orange residue. It was taken up in benzene, and chromatographically separated with a silica gel column eluting first with benzene, then with benzene-ethyl acetate solvent mixtures. The fractions containing the pure coupler were combined and the solvent removed in vacuo to give 2.6 g of coupler #31.

Using the same reaction scheme Couplers #32 and #33 were prepared:

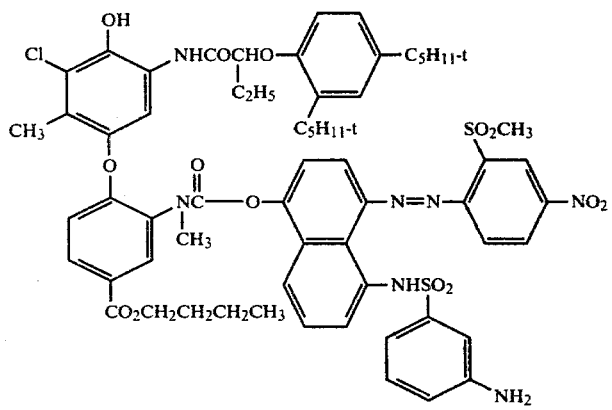

Coupler #32

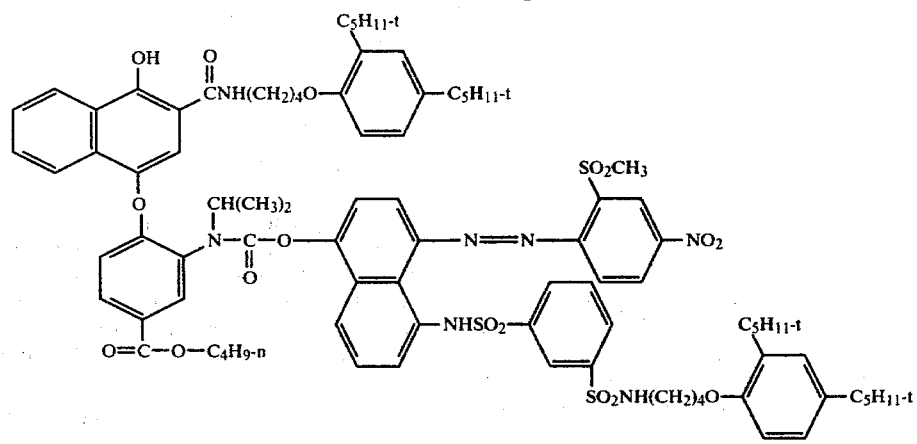

Coupler #33

PREPARATIVE EXAMPLE 5

Preparation of a Yellow Coupler Which Releases a Yellow Dye:

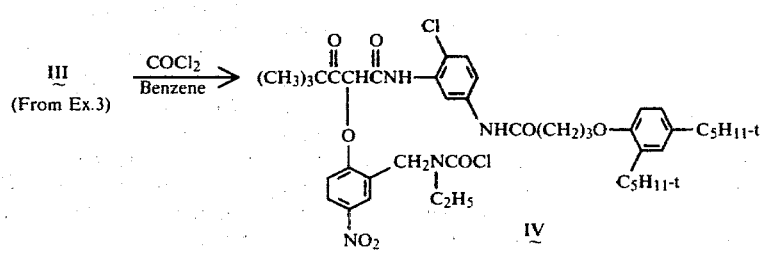

-continued

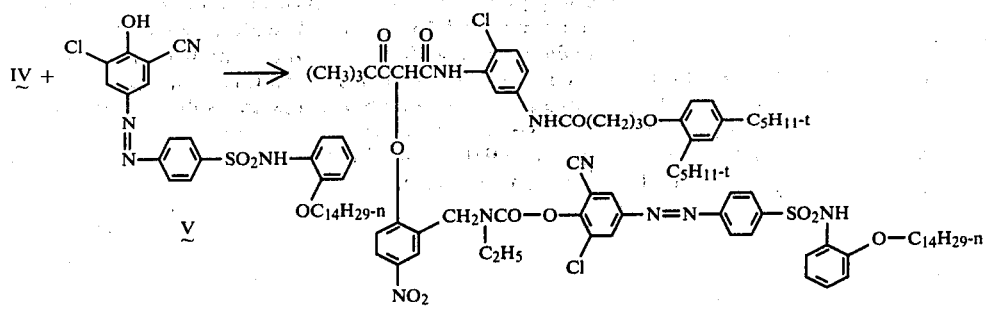

Coupler #34

Preparation of Compound V

To a stirred solution of 7.62 g of sulfanilic acid in 40 ml 2 N hydrochloric acid was added dropwise, at 0°–5° C., an ice-cold solution of 3.04 g of $NaNO_2$ in 20 ml water. The diazonium salt solution thus obtained was added dropwise to a solution of 6.14 g of 2-cyano-6-chlorophenol in 50 ml pyridine, maintaining the reaction temperature below 10° C. After the addition, the mixture was allowed to warm up slowly to room temperature, stirred for 2 more hours, and then cooled in an ice bath. The bright yellow solid which separated out was collected, washed with ice-cold water followed by cold acetone. Yield of the crude yellow azo dye was 15.4 g.

The product obtained above was added in small portions to a stirred solution of 500 g of thionyl chloride and 100 ml N,N-dimethylformamide at 0°–5° C. The mixture was stirred at this temperature for 4 hours and then poured into ice water. The orange solid which separated out was collected, washed twice with cold dilute hydrochloric acid and dried, dissolved in 700 ml ethyl acetate, dried over $Na_2SO_4$, filtered, and the solvent removed under reduced pressure to give 13 g of product; m.p. 209°–211° C.

The azophenol sulfonyl chloride derivative was added with stirring to a solution of 16 g of 2-tetradecyloxyaniline in 300 ml tetrahydrofuran and 50 g of di-isopropylethylamine at 0°–5° C. After the addition, the mixture was stirred at room temperature for 2 hours. It was poured into ice-water containing 100 ml concentrated hydrochloric acid. The solid was collected, washed with water, and dried. The crude dye was dissolved in 50 ml $CHCl_3$ and chromatographically separated with a silica gel column using a $CHCl_3$— ethyl acetate-acetic acid solvent mixture as eluant. A yield of 12 g of pure Compound V was obtained; m.p. 98°–100° C.

Preparation of Coupler #34

To a suspension of 12 g of Compound III of Example 2 in 500 ml benzene was added with stirring 100 ml of saturated $NaHCO_3$ solution. After stirring for 3 hours the organic phase was separated, dried over $MgSO_4$, filtered and the filtrate concentrated under reduced pressure to 100 ml. With stirring, 100 g of 12% solution of phosgene in benzene was added. The reaction mixture was stirred overnight, after which it was concentrated to dryness under reduced pressure. The residue was taken up in 20 ml tetrahydrofuran and reacted with 10.3 g of azophenol dye V dissolved in 500 ml pyridine. The reaction mixture was stirred at room temperature over the weekend.

It was poured into ice-water containing 60 ml concentrated hydrochloric acid. The brown solid was collected, washed with water, and dried. The crude coupler was dissolved in a minimum amount of $CHCl_3$ and purified by passing through a silica gel column using $CHCl_3$ and ethyl acetate as eluants. Yield of pure coupler #34: 9.2 g; m.p. 107°–110° C.

Using a similar procedure Coupler #'s 35, 36 and 37 were prepared:

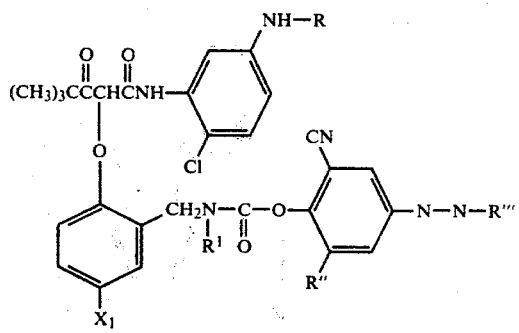
| Coupler # | X₁ | R | R' | R'' | R''' |
|---|---|---|---|---|---|
| 35 | —NO₂ | —C(=O)(CH₂)₃O-[3,5-di-C₅H₁₁-t-phenyl] | —C₂H₅ | —H | 3-methylphenyl-SO₂N(CH₃)(CH₂)₂N(CH₃)SO₂C₁₆H₃₃ |
| 36 | —NO₂ | —C(=O)(CH₂)₃O-[3,5-di-C₅H₁₁-t-phenyl] | —C₂H₅ | —Cl | 4-methylphenyl-SO₂NH-[3,5-bis(SO₂NHC₆H₁₃-n)phenyl] |
| 37 | —SO₂CH₃ | —C(=O)(CH₂)₃O-[3,5-di-C₅H₁₁-t-phenyl] | —CH₃ | —Cl | 4-methylphenyl-SO₂NH-[3,5-bis(SO₂NHC₆H₁₃-n)phenyl] |
PREPARATIVE EXAMPLE 6
Preparation of a Cyan Coupler Which Releases a Competing Coupler:
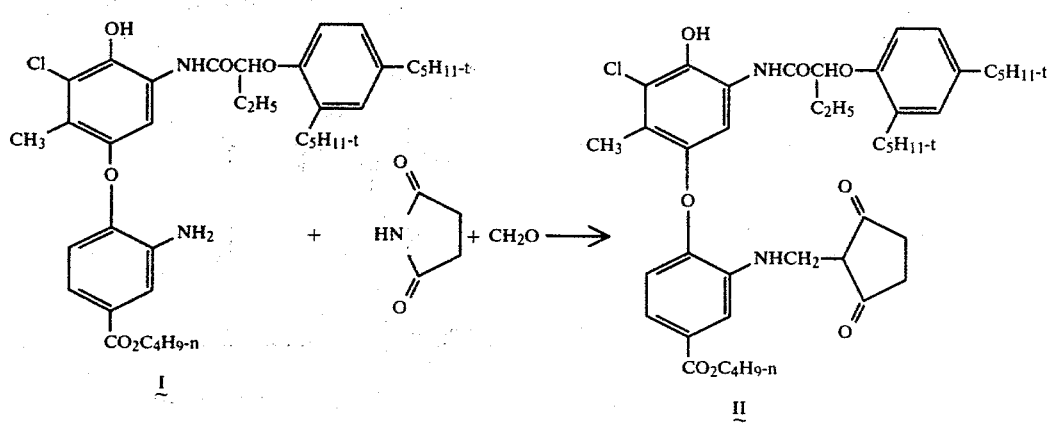

-continued

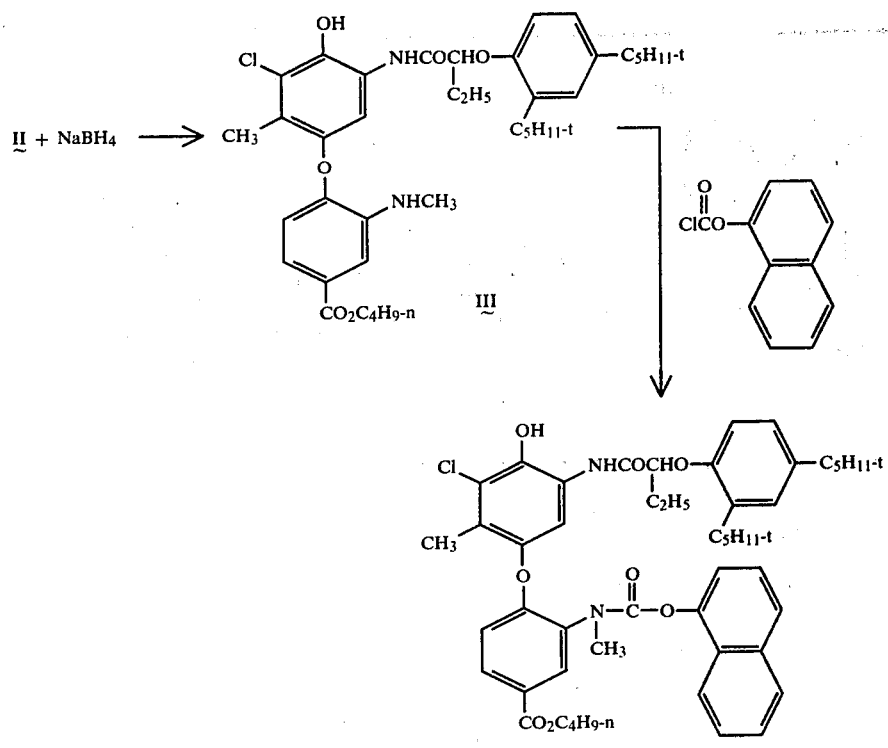

III

Coupler #38

Preparation of Compounds II and III

To a mixture of 26.7 g of compound I, 5.3 g of succinimide, 10 drops of trifluoroacetic acid and 240 ml of di-n-butyl ether heated at 100°–110° C., was added with stirring 1.7 g of paraformaldehyde. After heating for 1.5 hours, the mixture was cooled and the solvent was removed. The residue was taken up in dichloromethane and passed through a silica gel column to give 20 g of the succinimidomethyl derivative, compound II.

Compound II was dissolved in 100 ml of dimethylsulfoxide and warmed to 40° C. With stirring, 4.0 g of sodium borohydride was added in portions. It was then heated on a steam bath for 1.5 hours. The mixture was cooled and poured cautiously with stirring into 1.2 liters of ice water and 40 ml acetic acid. The white solid was collected, dissolved in 600 ml of dichloromethane, dried over MgSO$_4$ and filtered. The filtrate was passed through a short silica gel column using dichloromethane as the eluant. The solvent was removed under reduced pressure, and the residue was recrystallized from acetonitrile to give 10.7 g of pure compound III.

Preparation of Coupler #38

To a stirred solution of 4.6 g of compound III and 1.14 g of quinoline in 50 ml of tetrahydrofuran was added a solution of 1.6 g of 1-naphthylchloroformate in 20 ml tetrahydrofuran. The reaction mixture was stirred at ambient temperature for 3 hours, then poured into ice water containing 5 ml of concentrated HCl. The solid was collected, washed with water and dried. Recrystallization from acetonitrile gave 4.8 g of Coupler #38; m.p. 197°–199° C.

Using a similar procedure couplers 39 to 42 were prepared.

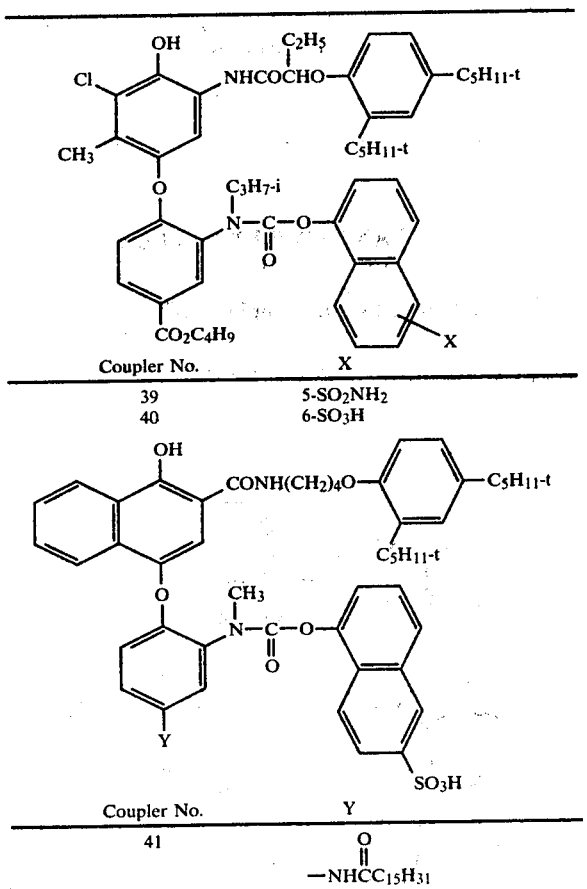

| Coupler No. | X |
|---|---|
| 39 | 5-SO$_2$NH$_2$ |
| 40 | 6-SO$_3$H |

| Coupler No. | Y |
|---|---|
| 41 | $-NHCC_{15}H_{31}$ with C=O |

| 42 |  |
|---|---|

PREPARATIVE EXAMPLE 7

Preparation of a Cyan Coupler Which Releases a Bleach Inhibitor:

Using a reaction procedure similar to that of preparative Example 1, Coupler 43 was prepared.

Coupler #43

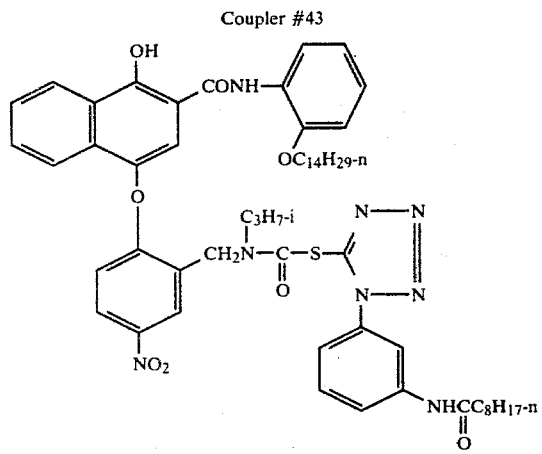

PREPARATIVE EXAMPLE 8

Preparation of Magenta Coupler Which Releases a Development Inhibitor:

Step 1

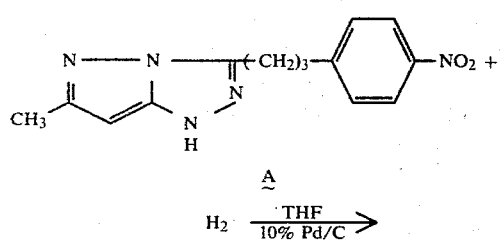

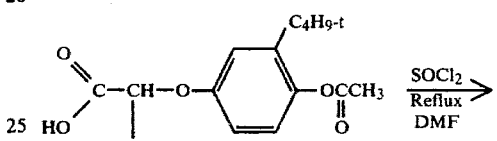

A mixture of 42.8 g (0.15 mol) of Compound A and 5 g of 10% palladium on carbon catalyst in 1 liter of dry tetrahydrofuran was reduced under 40 per square inch of hydrogen. After the theoretical amount of hydrogen was taken up, the reaction solution was heated to boiling and filtered hot to remove the catalyst. Concentration of the filtrate yielded 34.1 g of Compound B, m.p. 199°–200° C.

Step 2

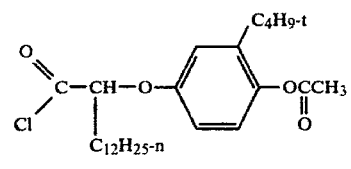

A mixture of 150.0 g (0.345 mol) of Compound C in 400 ml of thionyl chloride and six drops of N,N-dimethylformamide was refluxed for two hours. The excess thionyl chloride was removed under reduced pressure to give a dark brown oil. Toluene was added to the oil and the solvent again removed. After vacuum drying overnight, the oil was taken up in 500 ml of ligroin, treated with charcoal, filtered, and concentrated to 250 ml. Upon cooling in the refrigerator, the product crystallized into a solid mass. The solid product was collected, washed with cold ligroin, and vacuum dried to yield 132.3 g of Compound D, m.p. 49.5°–50° C.

Step 3

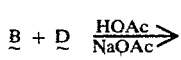

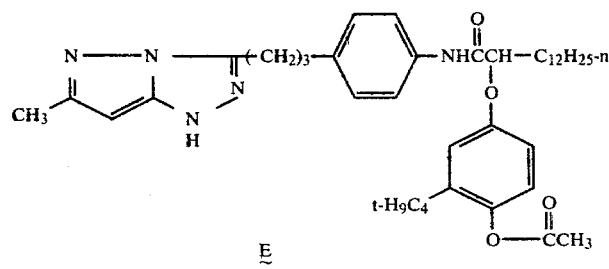

To a stirred suspension of 19.15 g (0.075 mol) of Compound B and 6.15 g (0.075 mol) of sodium acetate in 200 ml of glacial acetic acid was added a suspension of 33.98 g (0.075 mol) of Compound D in 50 ml glacial acetic acid. The reaction mixture was stirred for two hours at room temperature and then poured into ice water. The product was extracted with ethyl acetate. The organic extracts were washed repeatedly with water and 5% sodium bicarbonate solution. After drying over sodium sulfate, the solvent was removed under reduced pressure to give a brownish-yellow oil which was dissolved in a mixture of 230 ml of cyclohexane and 10 ml of ethyl acetate, seeded, and allowed to stand for about 48 hours. The crystallized product was collected, washed with hexane, and dried to yield 26.4 g of off-white powdery solid, Compound E, m.p. 123°–124° C.

Step 4

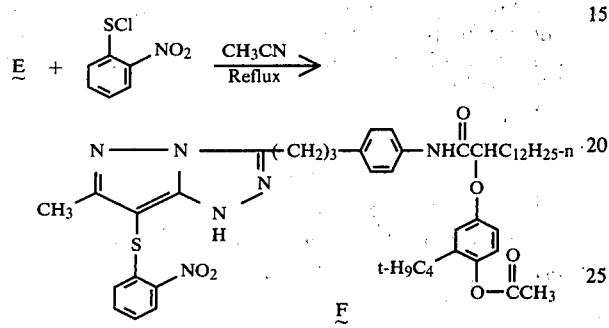

A mixture of 33.6 g (0.05 mol) of Compound E and 10.4 g (0.055 mol) of sulfenyl chloride in 500 ml dry acetonitrile was refluxed overnight. The solvent was removed under reduced pressure to give a reddish-brown gum which was partitioned between a mixture of 250 ml ethyl acetate, 150 ml ether, and aqueous 5% sodium bicarbonate solution. The organic phase was separated, washed twice with water, dried over sodium sulfate, and concentrated to a reddish-brown foamy solid. The material was recrystallized from 50 ml ethyl acetate and 250 ml hexane to yield 39.0 g yellow crystalline solid, Compound F, m.p. 88.5°–90° C.

Step 5

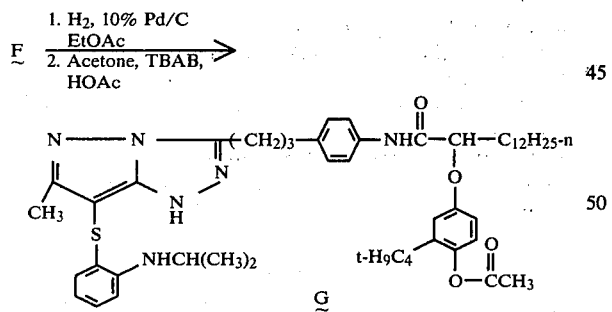

A mixture of 16.5 g (0.02 mol) Compound F and 6 g of 10% palladium on carbon in 250 ml ethyl acetate was reduced under 40 pounds per square inch of hydrogen. After the theoretical amount of hydrogen was taken up, the catalyst was filtered off and the solution was removed under reduced pressure. To the residual solid was added 11.6 g (0.2 mol) of acetone and 80 ml glacial acetic acid and the solution was cooled to about 15° C. After 15 minutes, a solution of 17.4 g (0.2 mol) of t-butyl-amine borane in 70 ml acetic acid was added dropwise, with stirring, over a 20 minute period. After three hours, the reaction mixture was poured with stirring into ice water. The resultant white solid was collected, washed with water, and vacuum dried over phosphorus pentoxide to yield 14.3 g of Compound G.

Step 6

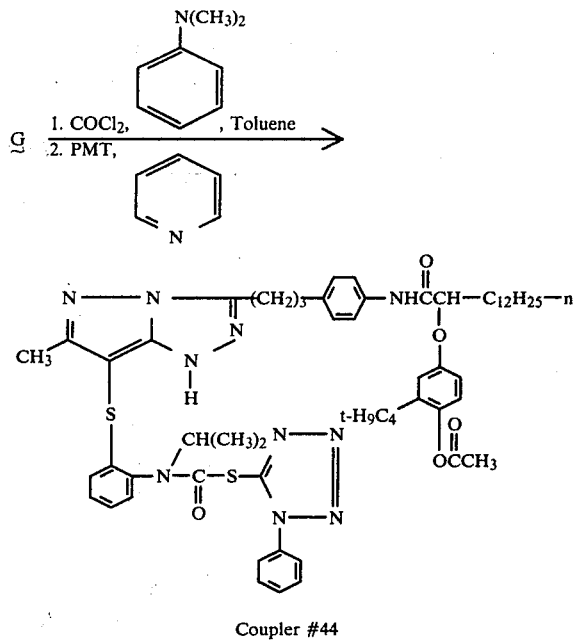

Coupler #44

A solution of 4.18 g (0.005 mol) of Compound G and 1.8 g (0.005 mol) of N,N-dimethylaniline in 50 ml toluene was cooled to about 0° C. With stirring, a two fold excess of a 12% solution of phosgene in toluene was added dropwise over a 45 minute period. The reaction mixture was stirred at room temperature overnight. Thin-layer chromatography indicated that little starting material remained. The toluene and excess phosgene were evaporated off and 75 ml of pyridine was added. To this was added dropwise, with stirring, 0.89 g (0.005 mol) of 1-phenyl-5-mercaptotetrazole in 30 ml pyridine. After stirring for five hours, the reaction mixture was poured with stirring into 500 ml of ice water containing 150 ml of concentrated hydrochloric acid and extracted with methylene chloride. The extracts were washed with water and aqueous saturated sodium chloride solution, dried over sodium sulfate, filtered and evaporated to yield 4.67 g of orange foamy solid. Elution with 10:1 methylene chloride-ethyl acetate from a column of silica gel isolated Coupler No. 44.

PREPARATIVE EXAMPLE 9

Preparation of a Coupler Which Yields a Colorless Reaction Product and Releases a Development Inhibitor.

Step 1

$n\text{-}C_{16}H_{33}SO_2NH$—[indanone]—Cl  +

1

-continued

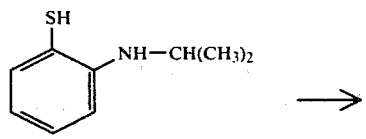

II

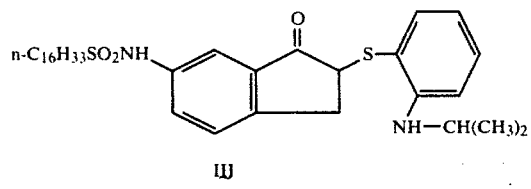

III

To 8.2 g (0.02 mol.) of 2-chloro-6-hexadecylsulfonamido indanone, suspended in 60 ml acetonitrile and 10 ml tetrahydrofuran, was added, at 0° C. with stirring, a solution of 3.7 g (0.022 mol.) of 2-isopropylaminobenzenethiol in 10 ml of tetrahydrofuran and 2.8 g (0.028 mol.) of triethylamine. The mixture was stirred for two hours and then poured into ice-water. The crude solid was collected, washed with water, and dried overnight.

Step 2

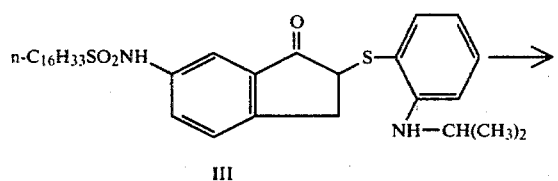

III

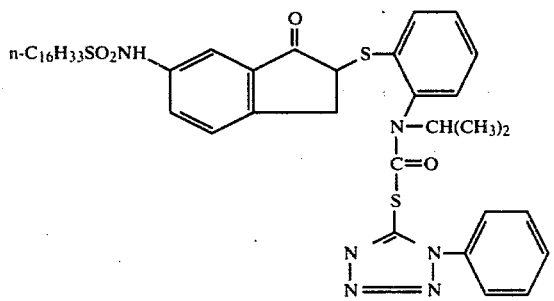

Coupler #45

To 50 ml of toluene saturated with phosgene was added, with stirring at 0° C., a solution of 5.1 g (0.009 mol.) of 2-(2'-isopropylaminophenylthio)-6-hexadecylsulfonamido indanone (Compound III) in 50 ml toluene and 1.2 g (0.0095 mol.) of dimethylaniline. After stirring at 0°-5° C. for two hours, the solvent was removed under reduced pressure. The residue was dissolved in 50 ml pyridine, and 1.7 g of phenylmercaptotetrazole was added. The reaction mixture was stirred for four hours at 0°-5° C. and then poured into ice-water. The oil was extracted with ethyl acetate, dried over magnesium sulfate, and the solvent was removed to give a brown oil. The crude product was chromatographed through a silica gel column to yield 3 grams of Coupler #45.

EXAMPLE 1.

Controlled Release of a Development Inhibitor

Four color photographic elements illustrated by the following schematic structure were prepared. The numerical values denote quantities in g/m².

| |
|---|
| Gelatin - 0.86 |
| AgX as Ag - 1.35; Cyan Dye Forming Coupler - 0.70; DIR Coupler - See below; Di-n-butyl phthalate - 0.5 g/ g total coupler; Gelatin - 2.7 |
| Film Support |

The cyan dye forming coupler has the formula:

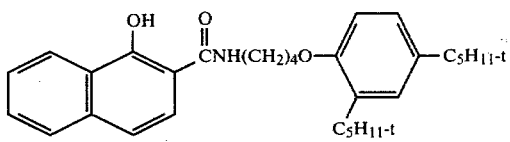

The elements contained development inhibitor releasing couplers as follows:

| Element | Coupler | g/m² | mol/m² |
|---|---|---|---|
| A (control) | None | — | — |
| B (control) | A* | 0.193 | 2.6 × 10⁻⁴ |
| C (invention) | #28 | 0.251 | 2.6 × 10⁻⁴ |
| D (invention) | #30 | 0.254 | 2.6 × 10⁻⁴ |

*Coupler A has the formula:

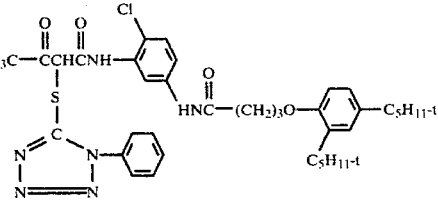

The four elements were exposed through a graduated-density test object, color developed in the composition described below for 2½ minutes at 38° C., bleached, fixed, and washed.

| Composition of Color Developer Solution: | |
|---|---|
| Water | |
| Diaminopropanol tetraacetic acid | 2.5 g |
| Hydroxylamine sulfate | 2.0 g |
| Na₂SO₃ (anhydrous) | 4.0 g |
| 4-Amino-3-methyl-N-ethyl-N-β-hydroxy-ethylaniline sulfate | 4.5 g |
| K₂CO₃ (anhydrous) | 37.5 g |
| NaBr | 1.4 g |
| KI | 0.002 g |
| Water to 1 liter; pH 10.0 | |

During color development oxidized color developing agent couples with the cyan dye forming coupler to produce cyan dye, and couples with DIR couplers A, 28 and 30 to produce yellow dye and release directly (coupler A) or indirectly (couplers 28 and 30) a development inhibitor. The release of development inhibitor during the course of color development affects the production of oxidized color developing agent, and hence affects the amount of dye produced. The effect is measured by plotting the density of red light (i.e., the density of the cyan dye produced) of each of the elements. These plots are shown in FIG. 1. It will be observed that for equivalent exposures the cyan density obtained with Element C is less than that obtained with control Element B and that the cyan density obtained with Element D is greater than that obtained with control Element B. This illustrates that merely by varying the timing group the time and rate of release of a development inhibiting can be controlled so that it can be released more rapidly (Element C) or more slowly (Element D) than the same development inhibitor released directly (Element B) from essentially the same coupler moiety.

EXAMPLE 2

Interimage Effects.

Five color photographic elements illustrated by the following schematic structure were prepared. The numerical values denote quantities in g/m$^2$.

| |
|---|
| Gelatin - 0.86 |
| Green-sensitive AgBrI - 1.6; Gelatin - 2.41; Cyan dye-forming coupler - 0.47; DIR coupler - See below; Di-n-butyl phthalate - 0.5 g/g total coupler Antistain agent - 2,5-Didodecylhydroquinone - 0.14; Gelatin 0.58 |
| Red-sensitive AgBrI - 1.6; Gelatin - 2.41; Yellow dye-forming coupler - 1.94; Di-n-butyl phthalate - 0.97 |
| Film Support |

The cyan dye-forming coupler was the same coupler as employed in the elements of Example 1. The yellow dye-forming coupler has the structure:

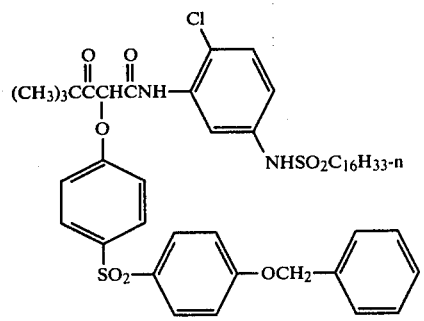

The elements contained development inhibitor releasing couplers as follows:

| Element | Coupler | g/m$^2$ | mol/m$^2$ |
|---|---|---|---|
| E | None | — | — |
| F | B | 0.09 | 1.4 × 10$^{-4}$ |
| G | 3 | 0.31 | 3.5 × 10$^{-4}$ |
| H | 4 | 0.09 | 1.0 × 10$^{-4}$ |
| I | 5 | 0.29 | 3.3 × 10$^{-4}$ |

The amount of development inhibitor releasing coupler incorporated in each of the elements was chosen to provide cyan dye curves having essentially equal slopes.

Coupler B has the structure:

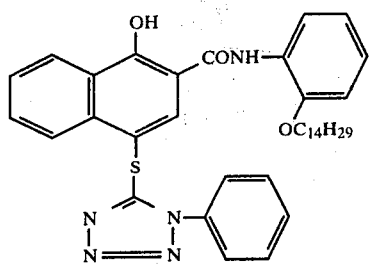

The five elements were exposed to green light through a graduated-density test object, then the test object was removed and the elements were uniformly flashed with red light. The elements were then color developed for 2 minutes at 38° C. using the composition described below, bleached, fixed and washed.

| Composition of Color Developer Solution: | |
|---|---|
| K$_2$SO$_3$ | 2.0 g |
| 4-Amino-3-methyl-N-ethyl-N-$\beta$-hydroxyethylaniline sulfate | 3.55 g |
| K$_2$CO$_3$ (anhydrous) | 30.0 g |
| KBr | 1.25 g |
| KI | 0.0006 g |
| Water to 1 liter | |
| pH to 11.0 | |

During color development oxidized color developing agent generated in the green-sensitive layer (which has been stepwise exposed) couples with the cyan dye-forming coupler and the DIR coupler to form cyan dye and releases directly (Coupler B) or indirectly (Couplers 3, 4 and 5) a development inhibitor. Oxidized color developing agent generated in the red-sensitive layer (which has been uniformly exposed) couples with the yellow dye-forming coupler to form yellow dye. Development inhibitor released from the couplers migrates through the element until, in its active form, it inhibits silver halide development and affects the amount of dye formed in both of the layers. The effect on the red sensitive layer is proportional to the amount of development inhibitor released in the green-sensitive layer and depends upon the amount of active development inhibitor reaching it. These effects are measured by plotting the densities of cyan dye (in the green-sensitive layer) and yellow dye (in the red-sensitive layer). These plots are shown in FIGS. 2-6. It will be observed that in each of Elements F-I, which contained development inhibitor releasing couplers, less yellow dye is formed in proportion to green exposure than in Element E which did not contain such a coupler; and that in Elements G-I, which contained couplers of this invention, significantly less yellow dye is formed in proportion to green exposure than in Element F, which contained a prior art coupler. This indicates that a greater amount of active development inhibitor is reaching the red-sensitive layer when couplers of this invention are employed than reaches the red-sensitive layer when couplers of the prior art are employed and results in greater interimage effects.

EXAMPLE 3

Release of a Yellow Image Dye

Three color photographic elements illustrated by the following schematic structure were prepared. The numerical values denote quantities in g/m².

| Gelatin - 0.54 | | | |
|---|---|---|---|
| Gelatin - 2.70; AgX As Ag - 1.62; Yellow dye-forming coupler - See below; Di-n-butyl phthalate - 0.5 (g/g coupler) | | | |
| Film Support | | | |
| Element | Coupler | g/m² | mol/m² |
| J (control) | C | 1.3 | 0.0158 |
| K (control) | C | 0.65 | 0.0078 |
| L | 34 | 0.65 | 0.0038 |

Coupler C has the structure:

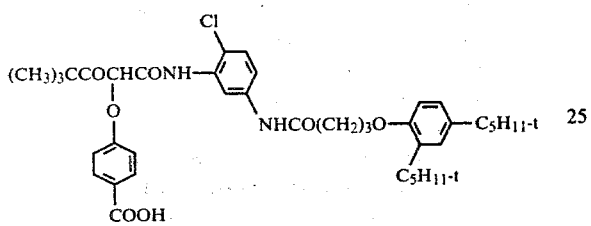

The elements were exposed through a graduated-density test object, and processed at 38° C. according to the following sequence:

| Processing Sequence: | |
|---|---|
| Color Developer | 2' |
| Water | |
| 4.3 g 4-Amino-3-methyl-N-ethyl-N-β-hydroxy-ethylaniline sulfate | |
| 0.1 ml H$_2$SO$_4$ | |
| 2.0 g Sodium hexametaphosphate | |
| 4.0 g Na$_2$SO$_3$ | |
| 20.0 g Na$_2$CO$_3$ . H$_2$O | |
| 2.0 g KBr | |
| Water to 1 liter, pH 11 | |
| Fix | 2' |
| 800 ml Water | |
| 240 g Na$_2$S$_2$O$_3$ . 5H$_2$O | |
| 15 g Na$_2$SO$_3$ | |
| 48 ml 28% Acetic Acid | |
| 7.5 g H$_2$BO$_3$ | |
| 15 g Potassium Alum | |
| Water to 1 liter, pH 4.25 | |
| Wash | 2' |
| Bleach | 2' |
| 21.5 g NaBr | |
| 100.0 g K$_3$Fe(CN)$_6$ | |
| 0.07 g NaH$_2$PO$_4$ . H$_2$O | |
| Water to 1 liter, pH to 7.0 | |
| Wash | 2' |
| Fix | 2' |
| (same as above) | |
| Wash | 2' |
| Stabilizing Solution | 2' |
| 5 g Cetyl trimethyl ammonium bromide | |
| 20 g Na$_2$CO$_3$ | |
| Water to 1 liter, pH 11 | |
| Wash | 10' |

Figure 7:
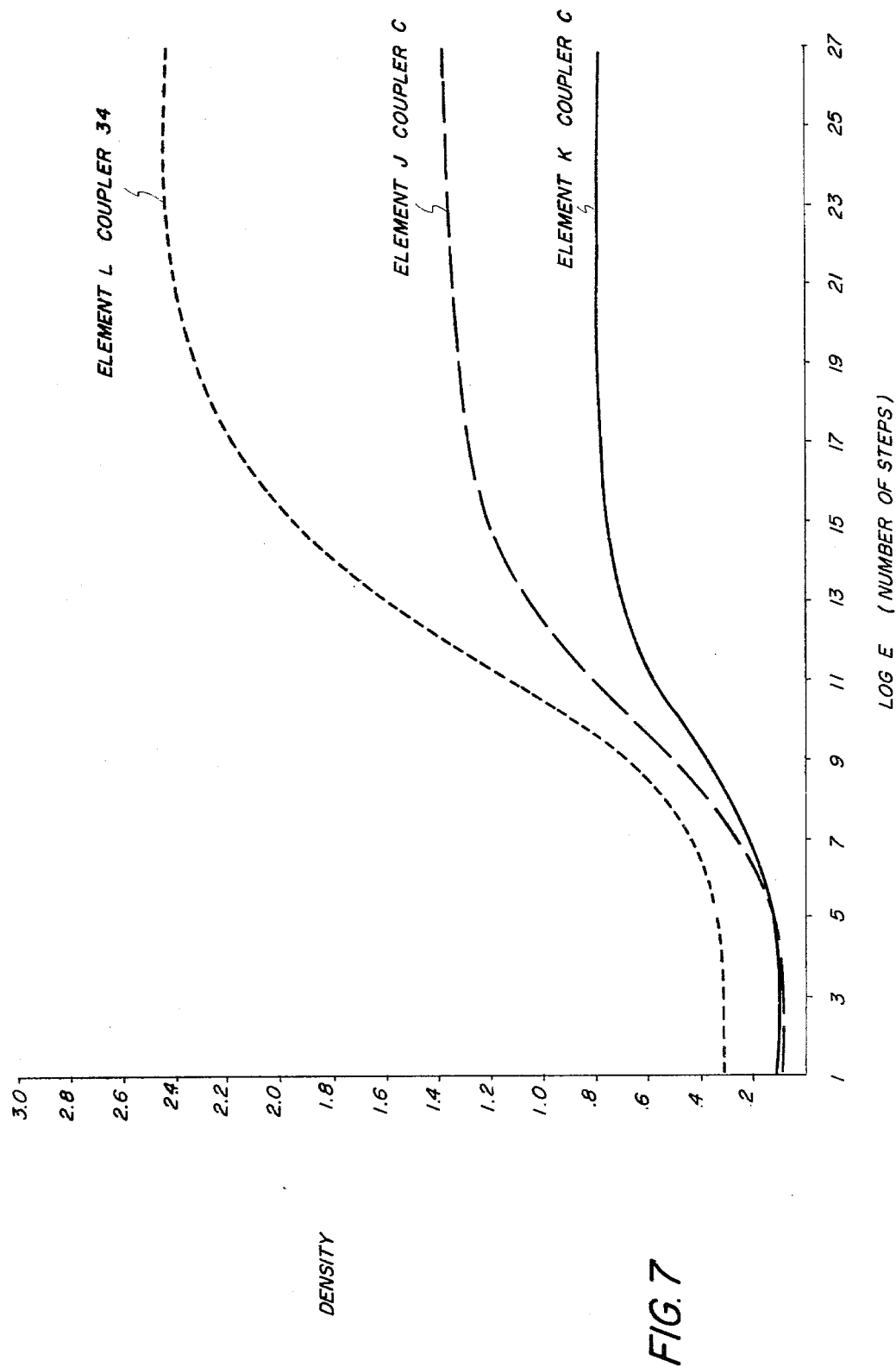

The resulting yellow dye images were evaluated by plotting yellow dye density vs. exposure. The results are shown in FIG. 7. It will be observed that Element L, of the invention, yielded significantly more dye density than the elements containing prior art dyes, even though it contained less yellow coupler.

EXAMPLE 4

Release of a Cyan Image Dye

Three color photographic elements illustrated by the following schematic structure were prepared. The numerical values denote quantities in g/m².

| Gelatin - 0.54; Hardener - 0.081 | | | |
|---|---|---|---|
| Red-sensitive AgX as Ag - 1.08; Cyan dye-forming coupler - See below; 2,4-di-n-amylphenol - 0.5 (g/g coupler); Gelatin - 2.70 | | | |
| Film Support | | | |
| Element | Coupler | g/m² | mol/m² |
| M | D | 0.86 | 0.0149 |
| N | D | 0.43 | 0.0075 |
| O | #31 | 1.40 | 0.0075 |

Coupler D has the structure:

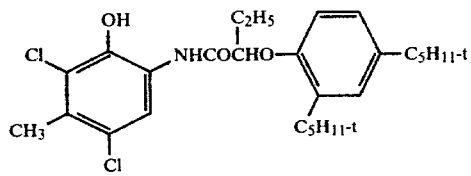

The elements were exposed and processed as in Example 3, except that the development was for 20 minutes at 20° C. in the following composition and that elements M and N were not treated in the cetyl trimethyl ammonium bromide solution:

| Composition of Color Developing Solution: | |
|---|---|
| Water | |
| K$_2$SO$_3$ | 2.0 g |
| 4-Amino-3-methyl-N-ethyl-N-β-(methanesulfonamido)ethyl-aniline sulfate hydrate | 5.0 g |
| Anhydrous K$_2$CO$_3$ | 30 g |
| KBr | 1.25 g |
| KI | 0.0006 g |
| Water to 1 liter | |
| pH to 11 | |

Figure 8:
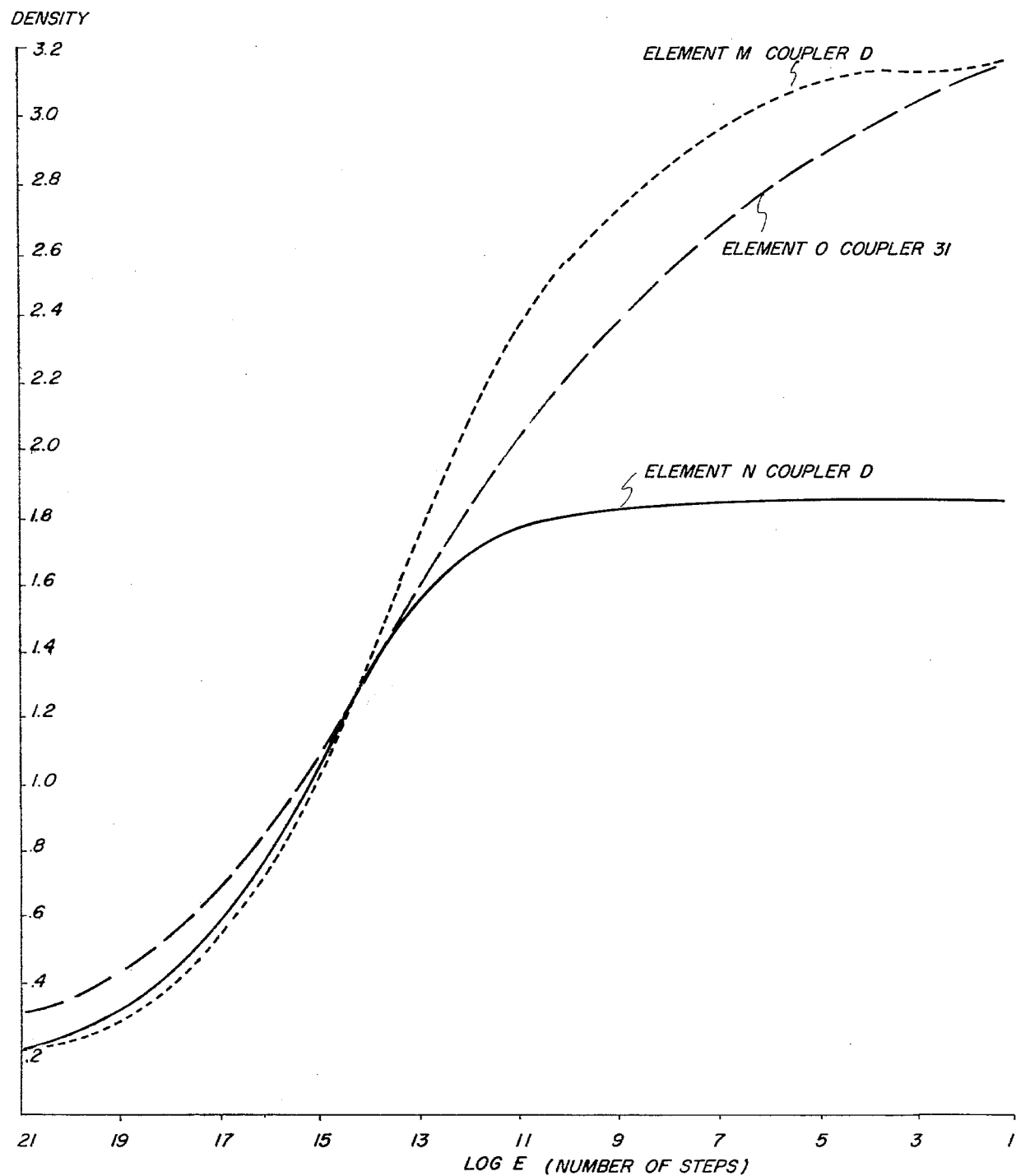

The resulting cyan dye images were evaluated by plotting cyan dye density vs. exposure. The results are shown in FIG. 8. It will be observed that Element O, according to this invention, yielded substantially more dye than Element N, which contained an equimolar amount of a prior art coupler.

EXAMPLE 5

Release of a Competing Coupler

Three color photographic elements illustrated by the following schematic structure were prepared. The numerical values denote quantity in g/m².

| Gelatin - 1.08 |
|---|
| AgBrI emulsion - see below/Coupler - see below/Tri-cresyl phosphate - 0.5 (g/g coupler); Gelatin 3.24 |
| Antihalation layer |

-continued

| | Film Support | | | |
|---|---|---|---|---|
| | | Cyan Dye-Forming | Coupler | |
| Element | AgBrI as Ag | Coupler | g/m² | mols/m² |
| P control | 1.08 | D (See Ex 4) | 0.26 | 0.0521 |
| Q | 1.08 | 38 | 0.48 | 0.052 |
| R | 3.24 | 38 | 0.48 | 0.052 |

Each element was exposed for 1/25 of a second through a neutral graduated-density test object and then processed at 38° C. according to the following sequence.

| Processing Sequence: | |
|---|---|
| Color developer | 1' |
| 2.0 g K₂SO₃ | |
| 2.45 g 4-Amino-3-methyl-N,N-diethyl-aniline hydrochloride | |
| 30.0 g K₂CO₃ (anhydrous) | |
| 1.25 g KBr | |
| 0.0006 g KI | |
| Water to 1 liter | |
| pH to 10.0 | |
| 10% Acetic Acid Stop | 4' |
| Bleach | 4' |
| 175 ml 1.56 Molar Ammonium Ferric Ethylenediamine tetraacetic acid | |
| 150 g NH₄Br | |
| 10.5 ml Acetic Acid | |
| 35 g NaNO₃ | |
| Water to 1 liter | |
| Wash | 3' |
| Fix | 4' |
| 162 ml 60% Ammonium thiosulphate solution | |
| 13 g Sodium Hydrogen Sulfite | |
| 2.83 ml 50% NaOH Solution | |
| Water to 1 liter | |
| Wash | 3' |
| Stabilizer | 1' |
| 10.0 ml 10% Wetting Agent | |
| 6.0 ml 35% Formalin | |
| Water to 1 liter | |

Figure 9:
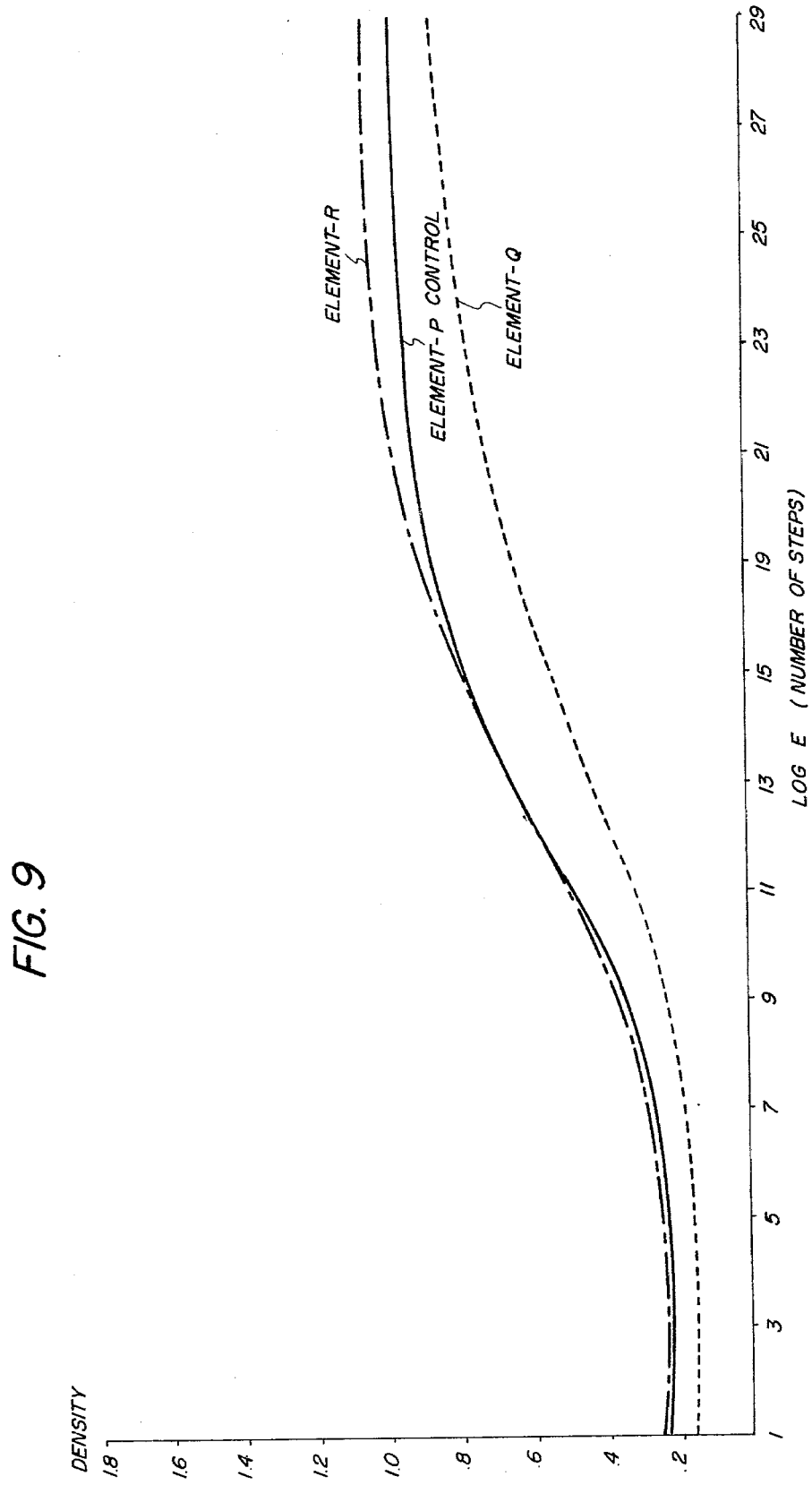

The resulting cyan dye images were evaluated by plotting cyan dye density vs exposure. The results are shown in FIG. 9. It will be observed that for equivalent amounts of silver (Elements P and Q) less dye density was obtained with a coupler of this invention than with a prior art coupler. In order to obtain equivalent density with a coupler of this invention approximately three times as much silver halide was required (Element R). Both of these observations indicate that competing coupler was being released and was competing for oxidized color developing agent with the cyan dye forming coupler.

EXAMPLE 6

Interimage Effects

Two multilayer color negative film elements identified by the following schematic structure were prepared. The numerical values denote quantities in g/m².

Gelatin Overcoat
Ultraviolet Protective Overcoat
Fast blue-sensitive, yellow-dye-forming silver halide emulsion layer; Blue-sensitive AgX as Ag - 0.93;

-continued

Yellow coupler (see Example 2) - 0.30 in di-n-butyl phthalate - 0.10; Gelatin - 0.61
Slow blue-sensitive, yellow dye-forming silver halide emulsion layer; Blue-sensitive AgX as Ag - 0.62;
Yellow coupler (see Example 2) - 1.25 in di-n-butyl phthalate - 0.42; Gelatin - 1.99
Yellow Colloidal Silver Filter Layer
Fast green-sensitive magenta-dye-forming silver halide emulsion layer; Green-sensitive AgX as Ag - 1.23; Magenta coupler (see below) - 0.098 in tricresylphosphate - 0.098; Colored magenta coupler (see below) - 0.03 in tricresylphosphate - 0.03; Gelatin - 0.63
Slow green-sensitive magenta-dye-forming silver halide emulsion layer; Green-sensitive AgX as Ag - 1.49; Magenta coupler (see below) - 0.59 in tricresylphosphate - 0.59; Colored magenta coupler (see below) - 0.092 in tricresylphosphate - 0.092 Magenta DIR coupler (see below) - 0.019 in tricresylphosphate - 0.039; Gelatin - 1.25
Gelatin Interlayer
Fast red-sensitive cyan-dye-forming silver halide emulsion layer; Red-sensitive AgX as Ag - 1.31; Cyan coupler (see Example 1) - 0.097 in di-n-butyl phthalate - 0.48; Colored cyan coupler (see below) - 0.004 in di-n-butyl phthalate - 0.002; Gelatin - 0.61
Slow red-sensitive cyan-dye-forming silver halide emulsion layer; Red-sensitive AgX as Ag - 2.26; Cyan coupler (see Example 1) - 0.59 in di-n-butyl phthalate - 0.29; Colored cyan coupler (see below) - 0.053 in di-n-butyl phthalate - 0.027; DIR coupler (see below); Gelatin - (see below)
Antihalation layer
Film Support The magenta coupler has the structure

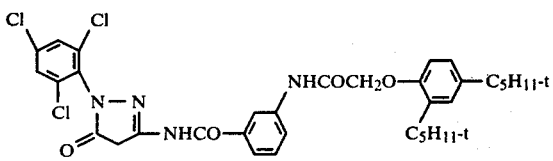

The colored magenta coupler has the structure

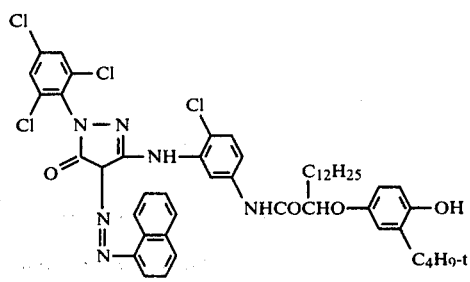

The magenta DIR coupler has the structure

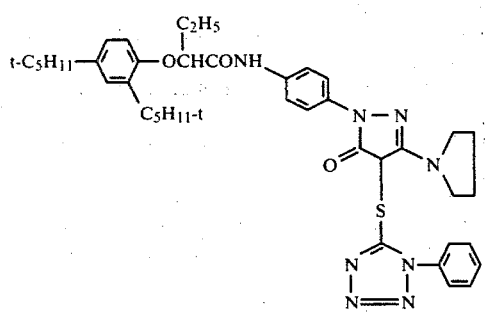

The colored cyan coupler has the structure

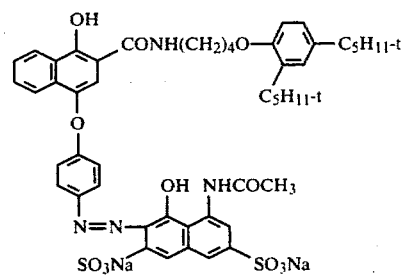

The elements contained in the slow red sensitive layer DIR coupler as follows. The amount of coupler was such as to provide similar D vs. Log E curves.

| Element | Coupler (g/m²) | Gelatin (g/m²) |
|---|---|---|
| S | B (See Ex. 2) — 0.029 in diethyl lauramide - 0.058 | 1.74 |
| T | #4 — 0.072 in N,n-butylacetanilide - 0.14 | 2.08 |

Each element was exposed for ¼ second, through a sinusoidal test pattern with a special frequency range of 2.5–100 cycles/mm, with a tungsten illuminant filtered to a color temperature of approximately 6500° K., color developed for 3¼ minutes at 38° C. in the composition shown in Example 1, bleached, fixed and washed.

The modulation transfer functions of the processed elements were then determined by the procedure described in the American National Standard Method for Determining the Photographic Modulation Transfer Function of Photographic Films, PH 2-33/7, January, 1973.

It was observed that element T (the invention) had improved cyan and magenta modulation transfer functions in the spatial frequency range of 10–40 cycles/mm, compared with element S (control). Thus, the couplers of this invention can provide multilayer elements of improved sharpness. For example, at 20 cycles/mm, in element T, the percent response of the cyan layer was about 108 and the percent response of the magenta layer was about 112, while in element S the comparable values were 90 and 100 percent.

EXAMPLE 7

Photographic elements similar to those of Example 2 were prepared having the following schematic structure:

| |
|---|
| Gelatin |
| Green-sensitive AgX gelatino emulsion layer containing a DIR coupler in 2 parts by weight of diethyl lauramide and a cyan-dye-forming coupler or a magenta-dye-forming coupler in ½ part by weight of di-n-butyl phthalate |
| Interlayer |
| Red-sensitive AgX gelatino emulsion layer containing a yellow dye forming coupler in ½ part by weight of di-n-butyl phthalate |
| Film Support |

The amount of DIR coupler in the green-sensitive layer was adjusted so that when that layer was stepwise exposed and processed, as described below, the density vs. log exposure plot had a slope ($\gamma$) of about 0.65. The following couplers, shown in the preparative examples were compared with analogous prior art couplers: Couplers 7, 13, 19, 23, 24 and 44. The elements were given a stepwise minus blue exposure, (using a Wratten 12 filter) color developed in the composition shown in Example 2 (but adjusted to pH 10) for 2¼ minutes at 38° C., fixed, bleached, fixed and washed. For each of the elements there was plotted the density, as a function of log exposure, of the red-sensitive layer (which contains yellow dye) to blue light and the density of the green-sensitive layer to red or green light (depending upon whether the dye-forming coupler yielded a cyan or magenta dye). The slope ($\gamma$) of the resultant curves was measured and the ratio between the slope of the curve for the green-sensitive layer and the slope of the curve for the red-sensitive layer ($\gamma_G/\gamma_R$) was calculated. This ratio is a measure of the interlayer interimage effect on the red-sensitive layer of development inhibitor released in the green-sensitive layer. Inasmuch as development inhibitor reaching the red-sensitive layer would reduce the slope of the density vs. log exposure curve for that layer, the greater the ratio $\gamma_G/\gamma_R$, the greater the interimage effect. It was observed that with the couplers of this invention the ratio $\gamma_G/\gamma_R$ was greater than that with analogous prior art couplers and thus the couplers of this invention provided a greater interimage effect than the analogous prior art couplers.

The elements were exposed to green light through a sinusoidal test pattern, as described in Example 6, processed as described above and modulation transfer function curves for the green sensitive layer were obtained as described in Example 6. From these curves it was observed that couplers of the present invention provided sharper images than analogous couplers of the prior art.

This invention has been described in detail with particular reference to preferred embodiments thereof, but it will be understood that variations and modifications can be effected within the spirit and scope of the invention.

We claim:

1. A photographic element comprising a support, at least one silver halide emulsion layer and a photographic coupler containing
    a coupler moiety,
    a photographic dye or reagent, containing a hetero atom from Group VA or VIA of the periodic table having a negative valence of 2 or 3 and
    a timing group joining the coupler moiety and the photographic dye or reagent, the timing means comprising a nucleophilic group attached to the coupler moiety at a position from which it is capable of being displaced as a result of reaction of the coupler moiety with oxidized color developing agent, an electrophilic group attached to said hetero atom in the photographic dye or reagent and capable of being displaced therefrom by said nucleophilic group after said nucleophilic group is displaced from said coupler moiety, and a linking group spatially relating the nucleophilic group and the electrophilic group to undergo, after cleavage of the bond between the timing group and the coupler moiety, an intramolecular nucleophilic displacement reaction which cleaves the bond between the photographic dye or reagent and the timing group.

2. A photographic element comprising a support, at least one silver halide emulsion layer and a photographic coupler represented by the structure:

$$\boxed{\text{COUP}}$$
$$|$$
$$\text{Nu}$$
$$|$$
$$\text{X}-\text{E}-\boxed{\text{PUG}}$$

where:
COUP is a coupler moiety;
PUG is a photographic dye or reagent containing a hetero atom from Group VA or VIA of the periodic table having a negative valence of 2 or 3;
Nu is a nucleophilic group containing an electron rich oxygen, sulfur or nitrogen atom, Nu being attached to a position on COUP from which it will be displaced upon reaction of COUP with oxidized color developing agent;
E is an electrophilic group containing an electron deficient carbonyl, thiocarbonyl, phosphinyl or thiophosphinyl moiety, E being attached to said hetero atom in PUG and being displaceable therefrom by Nu after Nu is displaced from COUP; and
X is a linking group for spatially relating Nu and E, upon displacement of Nu from COUP, to undergo an intramolecular nucleophilic displacement reaction with the formation of a three- to seven-membered ring and thereby release PUG.

3. A photographic element of claim 2, wherein PUG contains an oxygen, sulfur or heterocyclic nitrogen atom by which it is attached to E.

4. A photographic element of claim 2 wherein Nu contains an electron rich oxygen or sulfur atom; E contains an electron deficient carbonyl or thiocarbonyl group; PUG contains an oxgen or sulfur atom by which it is attached to E.

5. A photographic element of claim 2 wherein X is alkylene or an arylene linking group.

6. A photographic element of claim 2 wherein COUP is a coupler moiety which yields a colored product on reaction with oxidized color developing agent.

7. A photographic element of claim 2 wherein COUP is a coupler moiety which yields a colorless product on reaction with oxidized color developing agent.

8. A photographic element of claim 2 wherein PUG is a development inhibitor.

9. A photographic element of claim 2 wherein PUG is a dye or dye precursor.

10. A photographic element of claim 2 wherein PUG is a coupler.

11. A photographic element of claim 2 wherein PUG is a developing agent.

12. A photographic element of claim 2 wherein PUG is a bleach inhibitor.

13. A photographic element comprising a support and at least one silver halide emulsion layer having associated therewith a photographic coupler represented by the formula:

$$\boxed{\text{COUP}}$$
$$|$$
$$\text{Nu}$$

(with ring containing Z and E—PUG attachment)

where:
COUP is a coupler moiety;
Nu is a nucleophilic group attached to the coupling position of COUP, selected from the group consisting of $$-O-, -O-CR_2-, -O-\overset{O}{\underset{\|}{C}}-, -\overset{R}{\underset{|}{N}}-\overset{O}{\underset{\|}{C}}-, -S-,$$

$$-S-CR_2- \text{ and } -\overset{R}{\underset{|}{N}}-\overset{O}{\underset{\underset{O}{\|}}{S}}-$$

where R is hydrogen, alkyl of 1 to 20 carbon atoms aryl of 6 to 20 carbon atoms;

Z represents the atoms necessary to complete a mono- or bicyclic aromatic or heterocyclic ring system containing 5 to 10 ring atoms;

E is an electrophilic group selected from the group consisting of $$-(CR_2)_n-\overset{O}{\underset{\|}{C}}-, -(CR_2)_n-\overset{R}{\underset{|}{N}}-\overset{O}{\underset{\|}{C}}-, -(CR_2)_n-\overset{S}{\underset{\|}{C}}-, \text{ and}$$

$$-(CR_2)_n-\overset{R}{\underset{|}{N}}-\overset{O}{\underset{\|}{C}}-;$$

where each R is independently hydrogen, alkyl of 1 to 20 carbon atoms or aryl of 6 to 20 carbon atoms;

n is an integer of 0 to 4 such that the ring formed upon reaction of the nucleophilic center of Nu with the electrophilic center of E contains 5 to 6 members; and PUG is a photograhic dye or reagent containing a hetero atom from Group VA or VIA of the periodic table having a negative valence of 2 or 3 through which it is attached to a position on E from which it will be displaced upon nucleophilic attack of Nu at the electrophilic center in E.

14. A photographic element of claim 13 wherein COUP is a coupler moiety which yields a colored product on reaction with oxidized color developing agent.

15. A photographic element of claim 13 wherein COUP is a coupler moiety which yields a colorless or neutral product on reaction with oxidized color developing agent.

16. A photographic element comprising a support and at least one silver halide emulsion layer having associated therewith a photographic coupler represented by the structure

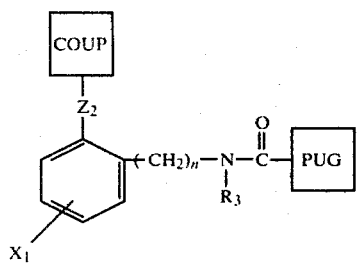

where:
COUP is a coupler moiety;
$Z_2$ is oxygen, or sulfur and is attached to the coupling position of COUP;
n is 0 or 1;
$R_3$ is hydrogen or alkyl of 1 to 4 carbon atoms or aryl of 6 to 10 carbon atoms;
PUG is a photographic dye or reagent containing an oxygen or sulfur atom by which it is attached to the carbonyl group; and
$X_1$ is hydrogen, halogen, cyano, nitro, alkyl of 1 to 20 carbon atoms, $-OR_4$, $-COOR_4$, $-CONHR_4$, $-NHCOR_4$, $-NHSO_2R_4$, $-SO_2NHR_4$ or $SO_2R_4$ where $R_4$ is hydrogen, alkyl of 1 to 20 carbon atoms or aryl of 6 to 20 carbon atoms.

17. A photographic element of claim 16 wherein COUP is a ballasted yellow-dye-forming coupler.

18. A photographic element of claim 16 wherein COUP is a ballasted cyan dye forming coupler.

19. A photographic element of claim 16 wherein COUP is a ballasted magenta dye forming coupler.

20. A photographic element of claim 16 wherein COUP forms a colorless reaction product on reaction with oxidized color developing agent.

21. A photographic element of claim 16 wherein PUG is a mercaptotetrazole or benzotriazole development inhibitor.

22. A photographic element comprising a support and at least one silver halide emulsion layer having associated therewith a photographic coupler represented by the structure:

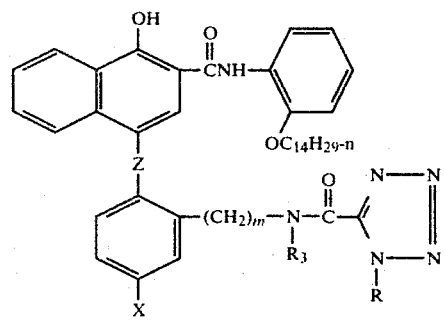

where:

Z is oxygen or sulfur;
X is hydrogen, nitro, alkoxycarbonyl, sulfonamido or carbonamido;
n is 0 or 1;
$R_3$ is alkyl of 1 to 4 carbon atoms and
R is phenyl or alkyl of 1 to 4 carbon atoms.

23. A photographic element comprising a support and at least one silver halide emulsion layer having associated therewith a photographic coupler represented by the structure:

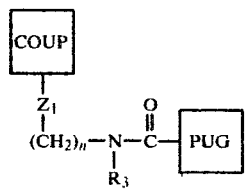

where:
COUP is a coupler moiety;
$Z_1$ is oxygen or sulfur and is attached to the coupling position of COUP;
n is 2 or 3;
$R_3$ is hydrogen, alkyl of 1 to 4 carbon atoms or aryl of 6 to 10 carbon atoms; and
PUG is a photographic dye or reagent containing an oxygen or sulfur atom by which it is attached to the carbonyl group.

24. A photographic element of claim 23 wherein COUP is a ballasted yellow-dye-forming coupler.

25. A photographic element of claim 23 wherein COUP is a ballasted cyan dye forming coupler.

26. A photographic element of claim 23 wherein COUP is a ballasted magenta dye forming coupler.

27. A photographic element of claim 23 wherein COUP forms a colorless reaction product on reaction with oxidized color developing agent.

28. A photographic element of claim 23 wherein PUG is a mercaptotetrazole or benzotriazole development inhibitor.

29. A photographic element comprising a support having thereon a red-sensitive silver halide emulsion unit having associated therewith a cyan-dye-image-providing material, a green-sensitive silver halide emulsion unit having associated therewith a magenta-dye-image-providing material, and a blue-sensitive silver halide emulsion unit having associated therewith a yellow-dye-image-providing material, at least one of the silver halide emulsion units having associated therewith a photographic coupler containing
   a coupler moiety,
   a photographic dye or reagent, containing a hetero atom from Group VA or VIA of the periodic table having a negative valence of 2 or 3 and
   a timing group joining the coupler moiety and the photographic dye or reagent, the timing group comprising
      a nucleophilic group attached to the coupler moiety at a position from which it is capable of being displaced as a result of reaction of the coupler moiety with oxidized color developing agent,
      an electrophilic group attached to said hetero atom in the photographic dye or reagent and capable of being displaced therefrom by said nucleophilic group after said nucleophilic group is displaced from said coupler moiety, and a linking group spatially relating the nucleophilic group and the electrophilic group to undergo, after cleavage of the bond between the timing group and the coupler moiety, an intramolecular nucleophilic displacement reaction which cleaves the bond between the photographic dye or reagent and the timing group.

30. A photographic element of claim 29 wherein the photographic coupler is represented by the structure

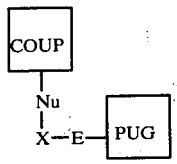

where:
COUP is a coupler moiety;
PUG is a photographically useful group containing a hetero atom from Group VA or VIA of the periodic table having a negative valence of 2 or 3;
Nu is a nucleophilic group containing an electron rich oxygen, sulfur or nitrogen atom, Nu being attached to a position on COUP from which it will be displaced upon reaction of COUP with oxidized color developing agent;
E is an electrophilic group containing an electron deficient carbonyl, thiocarbonyl, phosphinyl or thiophosphinyl moiety, E being attached to said hetero atom in PUG and being displaceable therefrom by Nu after Nu is displaced from COUP; and
X is a linking group for spatially relating Nu and E, upon displacement of Nu from COUP, to undergo an intramolecular nucleophilic displacement reaction with the formation of a three- to seven-membered ring and thereby release PUG.

31. A photographic element of claim 30, wherein PUG contains an oxygen, sulfur or heterocyclic nitrogen atom by which it is attached to E.

32. A photographic element of claim 30, wherein Nu contains an electron rich oxygen or sulfur atom; E contains an electron deficient carbonyl or thiocarbonyl group; and PUG contains an oxygen or sulfur atom by which it is attached to E.

33. A photographic element of claim 30, wherein X is alkylene or an arylene linking group.

34. A photographic element of claim 30, wherein said intramolecular nucleophilic displacement reaction involves the formation of a 5- or 6-membered ring.

35. A photographic element of claim 29 wherein the photographic coupler is represented by the structure

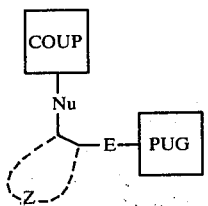

where:
COUP is a coupler moiety;

Nu is a nucleophilic group attached to the coupling position of COUP, selected from the group consisting of

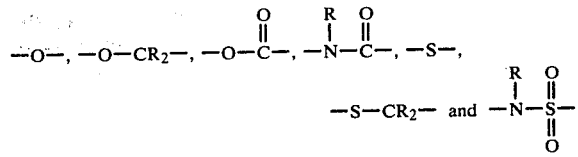

where R is hydrogen, alkyl of 1 to 20 carbon atoms or aryl of 6 to 20 carbon atoms;
Z represents the atoms necessary to complete a mono- or bicyclic aromatic or heterocyclic ring system containing 5 to 10 ring atoms;
E is an electrophilic group selected from the group consisting of

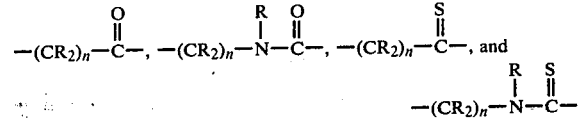

where each R is independently hydrogen, alkyl of 1 to 20 carbon atoms or aryl of 6 to 20 carbon atoms;
n is an integer of 0 to 4 such that the ring formed upon reaction of the nucleophilic center of Nu with the electrophilic center of E contains 5 to 6 members; and
PUG is a photographic dye or photographic reagent containing a hetero atom from Group VA or VIA of the periodic table having a negative valence of 2 or 3 through which it is attached to a position on E from which it will be displaced upon nucleophilic attack of Nu at the electrophilic center in E.

36. A photographic element of claim 35, wherein PUG contains an oxygen, sulfur or heterocyclic nitrogen atom by which it is attached to E.

37. A photographic element of claim 36 wherein PUG is a development inhibitor.

38. A photographic element of claim 36, wherein PUG is a dye or dye precursor.

39. A photographic element of claim 36, wherein PUG is a coupler.

40. A photographic element of claim 36, wherein PUG is a developing agent.

41. A photographic element of claim 36, wherein PUG is a bleach inhibitor.

42. A photographic element of claim 37, wherein PUG is a mercaptotetrazole or benzotriazole development inhibitor.

43. A photographic element of claim 37, wherein COUP is a coupler moiety which yields a colorless product on reaction with oxidized color developing agent.

44. A photographic element of claim 37, wherein COUP is a coupler moiety which yields a colored product on reaction with oxidized color developing agent.

45. A photographic element of claim 38, wherein PUG is a dye or dye precursor which on release from E in an alkaline photographic processing composition yields a dye of essentially the same color as the dye formed by reaction of COUP with oxidized color developing agent.

46. A photographic element of claim 29, wherein the photographic coupler is represented by the structure

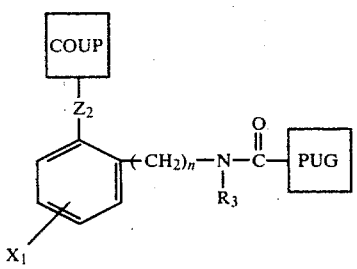

where:
COUP is a coupler moiety;
$Z_2$ is oxygen or sulfur and is attached to the coupling position of COUP;
n is 0 or 1;
$R_3$ is hydrogen, alkyl of 1 to 4 carbon atoms or aryl of 6 to 10 carbon atoms;
PUG is a photographic dye or photographic reagent containing an oxygen or sulfur atom by which it is attached to the carbonyl group; and
$X_1$ is hydrogen, halogen, cyano, nitro, alkyl of 1 to 20 carbon atoms, $-OR_4$, $-COOR_4$, $-CONHR_4$, $-NHCOR_4$, $-NHSO_2R_4$, $-SO_2NHR_4$ or $SO_2R_4$ where $R_4$ is hydrogen, alkyl of 1 to 20 carbon atoms or aryl of 6 to 20 carbon atoms.

47. A photographic element of claim 29 wherein the photographic coupler is represented by the structure

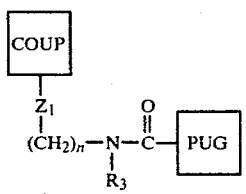

where:
COUP is a coupler moiety;
$Z_1$ is oxygen or sulfur and is attached to the coupling position of COUP;
n is 2 or 3;
$R_3$ is hydrogen, alkyl of 1 to 4 carbon atoms or aryl of 6 to 10 carbon atoms; and
PUG is a photographic dye or reagent containing an oxygen or sulfur atom by which it is attached to the carbonyl group.

48. A photographic element of claim 39 wherein the photographic coupler and the dye forming coupler yield dyes of essentially the same color on reaction with oxidized color developing agent.

49. A photographic element of claim 39 wherein the photographic coupler and the dye forming coupler yield dyes of different color on reaction with oxidized color developing agent.

50. A silver halide emulsion containing a photographic coupler having
a coupler moiety,
a photographic dye or reagent, containing a hetero atom from Group VA or VIA of the periodic table having a negative valence of 2 or 3 and
a timing group joining the coupler moiety and the photographic dye or reagent, the timing group comprising
a nucleophilic group attached to the coupler moiety at a position from which it is capable of being displaced as a result of reaction of the coupler moiety with oxidized color developing agent,
an electrophilic group attached to said hetero atom in the photographic dye or reagent and capable of being displaced therefrom by said nucleophilic group after said nucleophilic group is displaced from said coupler moiety, and
a linking group spatially relating the nucleophilic group and the electrophilic group to undergo, after cleavage of the bond between the timing group and the coupler moiety, an intramolecular nucleophilic displacement reaction which cleaves the bond between the photographic dye or reagent and the timing group.

51. A photograhic silver halide emulsion containing a photographic coupler represented by the structure:

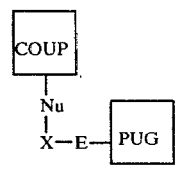

where:
COUP is a coupler moiety;
PUG is a photograhic dye or reagent containing a hetero atom from Group VA or VIA of the periodic table having a negative valence of 2 or 3;
Nu is a nucleophilic group containing an electron rich oxygen, sulfur or nitrogen atom, Nu being attached to a position on COUP from which it will be displaced upon reaction of COUP with oxidized color developing agent;
E is an electrophilic group containing an electron deficient carbonyl, thiocarbonyl, phosphinyl or thiophosphinyl moiety, E being attached to said hetero atom in PUG and being displacable therefrom by Nu after Nu is displaced from COUP; and
X is a linking group for spatially relating Nu and E, upon displacement of Nu from COUP, to undergo an intramolecular nucleophilic displacement reaction with the formation of a three- to seven-membered ring and thereby release PUG.

52. A photographic silver halide emulsion containing a photographic coupler represented by the formula:

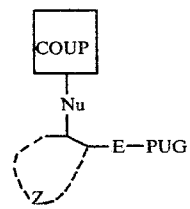

where:
COUP is a coupler moiety;
Nu is a nucleophilic group attached to the coupling position of COUP, selected from the group consisting of

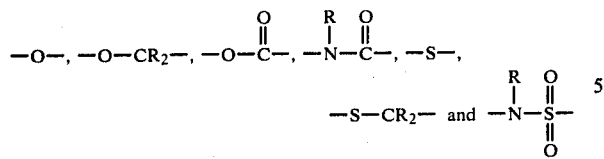

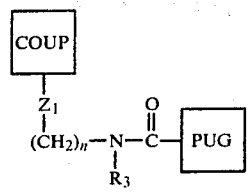

where R is hydrogen, alkyl of 1 to 20 carbon atoms or aryl of 6 to 20 carbon atoms;

Z represents the atoms necessary to complete a mono- or bicyclic aromatic or heterocyclic ring system containing 5 to 10 ring atoms;

E is an electrophilic group selected from the group consisting of

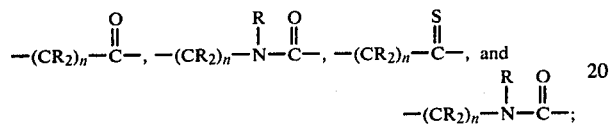

where each R is independently hydrogen, alkyl of 1 to 20 carbon atoms or aryl of 6 to 20 carbon atoms;

n is an integer of 0 to 4 such that the ring formed upon reaction of the nucleophilic center of Nu with the electrophilic center of E contains 5 to 6 members; and PUG is a photograhic dye or reagent containing a hetero atom from Group VA or VIA of the periodic table having a negative valence of 2 or 3 through which it is attached to a position on E from which it will be displaced upon nucleophilic attack of Nu at the electrophilic center in E.

53. A photographic silver halide emulsion containing a photographic coupler represented by the structure:

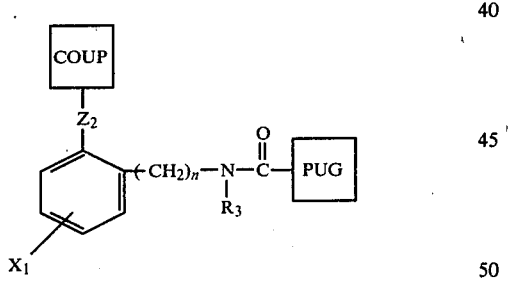

where:
COUP is a coupler moiety;
$Z_2$ is oxygen, or sulfur and is attached to the coupling position of COUP;
n is 0 or 1;
$R_3$ is hydrogen, alkyl of 1 to 4 carbon atoms or aryl of 6 to 10 carbon atoms;
PUG is a photographic dye or reagent containing an oxygen or sulfur atom by which it is attached to the carbonyl group; and
$X_1$ is hydrogen, halogen, cyano, nitro, alkyl of 1 to 20 carbon atoms, $-OR_4$, $-COOR_4$, $-CONHR_4$, $-NHCOR_4$, $-NHSO_2R_4$, $-SO_2NHR_4$ or $SO_2R_4$ where $R_4$ is hydrogen, alkyl of 1 to 20 carbon atoms or aryl of 6 to 20 carbon atoms.

54. A photographic silver halide emulsion containing a photographic coupler represented by the structure:

where:
COUP is a coupler moiety;
$Z_1$ is oxygen or sulfur and is attached to the coupling position of COUP;
n is 2 or 3;
$R_3$ is hydrogen, alkyl of 1 to 4 carbon atoms or aryl of 6 to 10 carbon atoms; and
PUG is a photographic dye or reagent containing an oxygen or sulfur atom by which it is attached to the carbonyl group.

55. A process of forming a photographic image which comprises developing an exposed silver halide emulsion layer with a color developing agent in the presence of a photographic coupler wherein the photographic coupler contains
a coupler moiety,
a photographic dye or reagent, containing a hetero atom from Group VA or VIA of the periodic table having a negative valence of 2 or 3 and
a timing group joining the coupler moiety and the photographic dye or reagent, the timing group comprising
a nucleophilic group attached to the coupler moiety at a position from which it is capable of being displaced as a result of reaction of the coupler moiety with oxidized color developing agent,
an electrophilic group attached to said hetero atom in the photographic dye or reagent and capable of being displaced therefrom by said nucleophilic group after said nucleophilic group is displaced from said coupler moiety, and
a linking group spatially relating the nucleophilic group and the electrophilic group to undergo, after cleavage of the bond between the timing group and the coupler moiety, an intramolecular nucleophilic displacement reaction which cleaves the bond between the photographic dye or reagent and the timing group.

56. A process of claim 55 wherein the photographic coupler is represented by the structure:

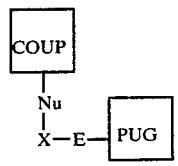

where:
COUP is a coupler moiety;
PUG is a photographic dye or reagent containing a hetero atom from Group VA or VIA of the periodic table having a negative valence of 2 or 3;
Nu is a nucleophilic group containing an electron rich oxygen, sulfur or nitrogen atom, Nu being attached to a position on COUP from which it will be displaced upon reaction of COUP with oxidized color developing agent;

E is an electrophilic group containing an electron deficient carbonyl, thiocarbonyl, phosphinyl or thiophosphinyl moiety, E being attached to said hetero atom in PUG and being displaceable therefrom by Nu after Nu is displaced from COUP; and X is a linking group for spatially relating Nu and E, upon displacement of Nu from COUP, to undergo an intramolecular nucleophilic displacement reaction with the formation of a three- to seven-membered ring and thereby release PUG.

57. A process of claim 55 wherein the photographic coupler is represented by the formula

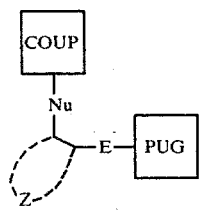

where:

COUP is a coupler moiety;

Nu is a nucleophilic group attached to the coupling position of COUP, selected from the group consisting of

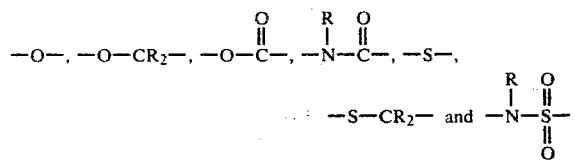

where R is hydrogen, alkyl of 1 to 20 carbon atoms or aryl of 6 to 20 carbon atoms;

Z represents the atoms necessary to complete a mono- or bicyclic aromatic or heterocyclic ring system containing 5 to 10 ring atoms;

E is an electrophilic group selected from the group consisting of

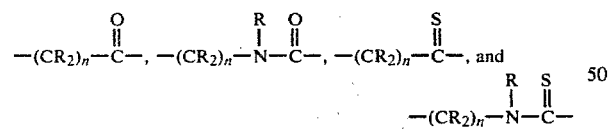

where each R is independently hydrogen or alkyl of 1 to 20 carbon atoms or aryl of 6 to 20 carbon atoms;

n is an integer of 0 to 4 such that the ring formed upon reaction of the nucleophilic center of Nu with the electrophilic center of E contains 5 to 6 members; and PUG is a photographic dye or reagent containing a hetero atom from Group VA or VIA of the periodic table having a negative valence of 2 or 3 through which it is attached to a position on E from which it will be displaced upon nucleophilic attack of Nu at the electrophilic center in E.

58. A process of claim 57 wherein the photographic coupler is contained in the photographic element.

59. A process of claim 57 wherein the photographic coupler is contained in a processing solution with the color developing agent.

60. A photographic element comprising a support, at least one silver halide emulsion layer and a photographic coupler containing a coupler moiety, a photographic dye or reagent, containing a hetero atom from Group VA or VIA of the periodic table having a negative valence of 2 or 3 and a timing group joining the coupler moiety and the photographic dye or reagent, the timing group comprising a nucleophilic group attached to the coupler moiety at a position from which it is capable of being displaced as a result of reaction of the coupler moiety with oxidized color developing agent, an electrophilic group attached to said hetero atom in the photographic dye or reagent and capable of being displaced therefrom by said nucleophilic group after said nucleophilic group is displaced from said coupler moiety, and a linking group spatially relating the nucleophilic group and the electrophilic group to undergo, after cleavage of the bond between the timing group and the coupler moiety, an intramolecular nucleophilic displacement reaction, with the formation of a five- or six-membered ring, which cleaves the bond between the photographic dye or reagent and the timing group.

61. A photographic element comprising a support, at least one silver halide emulsion layer and a photographic coupler represented by the structure:

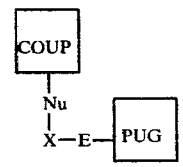

where:

COUP is a coupler moiety;

PUG is a photographic dye or reagent containing a hetero atom from Group VA or VIA of the periodic table having a negative valence of 2 or 3;

Nu is a nucleophilic group containing an electron rich oxygen, sulfur or nitrogen atom, Nu being attached to a position on COUP from which it will be displaced upon reaction of COUP with oxidized color developing agent;

E is an electrophilic group containing an electron deficient carbonyl, thiocarbonyl, phosphinyl or thiophosphinyl moiety, E being attached to said hetero atom in PUG and being displaceable therefrom by Nu after Nu is displaced from COUP; and X is a linking group for spatially relating Nu and E, upon displacement of Nu from COUP, to undergo an intramolecular nucleophilic displacement reaction with the formation of a five- or six-membered ring and thereby release PUG.

62. A photographic element comprising a support and at least one silver halide emulsion layer having associated therewith a photographic coupler represented by one of the structures:

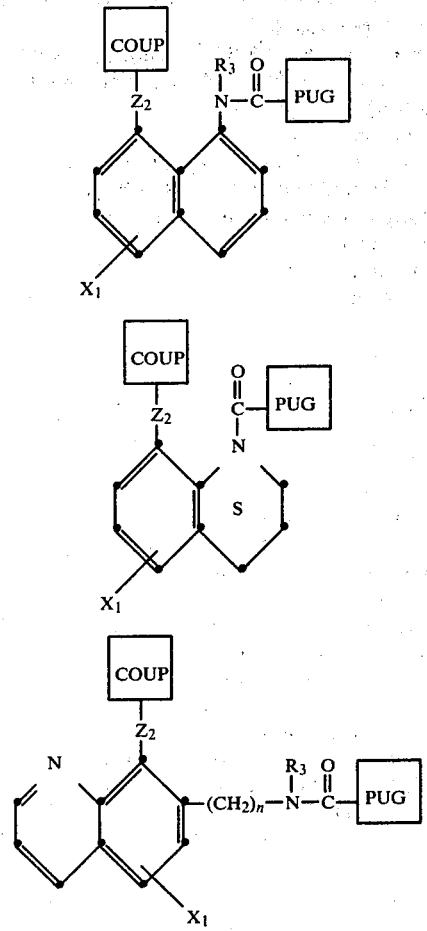

where:
COUP is a coupler moiety;
$Z_2$ is

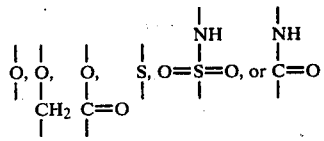

and is attached to the coupling position of COUP;
n is 0 or 1;
$R_3$ is hydrogen or alkyl of 1 to 20 carbon atoms or aryl of 6 to 20 carbon atoms;
PUG is a photographic dye or reagent containing an oxygen or sulfur atom by which it is attached to the carbonyl group; and
$X_1$ is hydrogen, halogen, cyano, nitro, alkyl of 1 to 20 carbon atoms, $-OR_4$, $-COOR_4$, $-CONHR_4$, $-NHCOR_4$, $-NHSO_2R_4$, $-SO_2NHR_4$ or $SO_2R_4$ where $R_4$ is hydrogen, alkyl of 1 to 20 carbon atoms or aryl of 6 to 20 carbon atoms.

63. A photographic element comprising a support and at least one silver halide emulsion layer having associated therewith a photographic coupler represented by one of the structures:

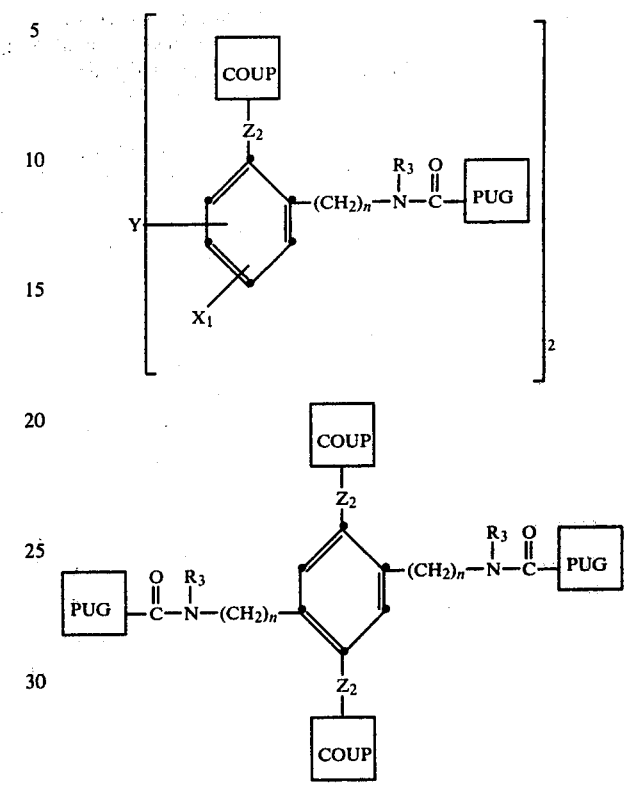

where:
COUP is a coupler moiety;
Y is

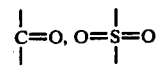

or $-NHSO_2CH_2SO_2NH-$;
$Z_2$ is

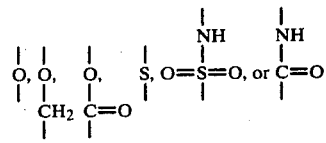

and is attached to the coupling position of COUP;
n is 0 or 1;
$R_3$ is hydrogen or alkyl of 1 to 20 carbon atoms or aryl of 6 to 20 carbon atoms;
PUG is a photographic dye or reagent containing an oxygen or sulfur atom by which it is attached to the carbonyl group; and
$X_1$ is hydrogen, halogen, cyano, nitro, alkyl of 1 to 20 carbon atoms, $-OR_4$, $-COOR_4$, $-CONHR_4$, $-NHCOR_4$, $-NHSO_2R_4$, $-SO_2NHR_4$ or $SO_2R_4$ where $R_4$ is hydrogen, alkyl of 1 to 20 carbon atoms or aryl of 6 to 20 carbon atoms.

* * * * *

UNITED STATES PATENT OFFICE
CERTIFICATE OF CORRECTION

Patent No. 4,248,962                    Dated February 3, 1981

Inventor(s) Philip T. S. Lau

It is certified that error appears in the above-identified patent and that said Letters Patent are hereby corrected as shown below:

Column 5, line 65, "at" should be ---to---.

Column 8, line 54, "-O-CR$_2$-" should be --- -O-, -O-CR$_2$- ---.

Column 12, line 37, "Acrylic" should be ---Acyclic---.

Column 31, coupler #31, the first ring in the structure

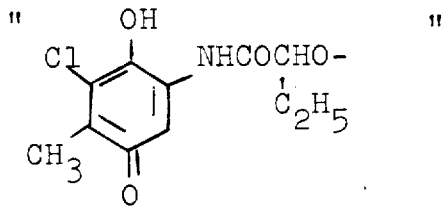

should read

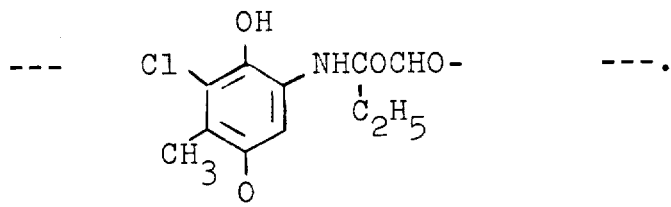

Column 47, line 10, "inhibiting" should be ---inhibitor---.

UNITED STATES PATENT OFFICE
CERTIFICATE OF CORRECTION

Patent No. 4,248,962　　　　　　　　Dated February 3, 1981

Inventor(s) Philip T. S. Lau

It is certified that error appears in the above-identified patent and that said Letters Patent are hereby corrected as shown below:

Column 47, lines 22-30,

"

| Gelatin - 0.86 |
| --- |
| Green-sensitive AgBrI - 1.6; Gelatin - 2.41; Cyan dye-forming coupler - 0.47; DIR coupler - See below. Di-n-butyl phthalate - 0.5 g/g total coupler |
| Antistain agent - 2,5-Didodecylhydroquinone - 0.14; Gelatin 0.58 |
| Red-sensitive AgBrI - 1.6; Gelatin - 2.41; Yellow dye-forming coupler - 1.94; Di-n-butyl phthalate - 0.97 |
| Film Support |

"

should be

---

| Gelatin - 0.86 |
| --- |
| Green-sensitive AgBrI - 1.6; Gelatin - 2.41; Cyan dye-forming coupler - 0.47; DIR coupler - See below. Di-n-butyl phthalate - 0.5 g/g total coupler |
| Antistain agent - 2,5-Didodecylhydroquinone - 0.14; Gelatin 0.58 |
| Red-sensitive AgBrI - 1.6; Gelatin - 2.41; Yellow dye-forming coupler - 1.94, Di-n-butyl phthalate - 0.97 |
| Film Support |

---

UNITED STATES PATENT OFFICE
CERTIFICATE OF CORRECTION

Patent No. 4,248,962   Dated February 3, 1981

Inventor(s) Philip T. S. Lau

It is certified that error appears in the above-identified patent and that said Letters Patent are hereby corrected as shown below:

Column 49, lines 7-12,

"
| |
|---|
| Gelatin - 0.54 |
| Gelatin - 2.70. AgX As Ag - 1.62. Yellow dye-forming coupler - See below Di-n-butyl phthalate - 0.5 (g/g coupler) |
| Film Support |

"

should be

---
| |
|---|
| Gelatin - 0.54 |
| Gelatin - 2.70. AgX As Ag - 1.62. Yellow dye-forming coupler - See below Di-n-butyl phthalate - 0.5 (g/g coupler) |
| Film Support |

---.

Column 50, lines 11-20,

"
| |
|---|
| Gelatin - 0.54; Hardener - 0.081 Red-sensitive AgX as Ag - 1.08; Cyan dye-forming coupler - See below; 2,4-di-n-amylphenol - 0.5 (g/g coupler); Gelatin - 2.70 |
| Film Support |

"

should be

---
| |
|---|
| Gelatin - 0.54; Hardener - 0.081 Red-sensitive AgX as Ag - 1.08; Cyan dye-forming coupler - See below; 2,4-di-n-amylphenol - 0.5 (g/g coupler); Gelatin - 2.70 |
| Film Support |

---.

UNITED STATES PATENT OFFICE
CERTIFICATE OF CORRECTION

Patent No. 4,248,962  Dated February 3, 1981

Inventor(s) Philip T. S. Lau

It is certified that error appears in the above-identified patent and that said Letters Patent are hereby corrected as shown below:

Column 50, line 65 through column 51, line 3

"

| Gelatin - 1.08 |
|---|
| AgBrI emulsion - see below/Coupler - see below/Tri-cresyl phosphate - 0.5 (g/g coupler); Gelatin 3.24 |
| Antihalation layer |
| Film Support |

"

should be

---

| Gelatin - 1.08 |
|---|
| AgBrI emulsion - see below/Coupler - see below/Tri-cresyl phosphate - 0.5 (g/g coupler); Gelatin 3.24 |
| Antihalation layer |
| Film Support |

---.

Column 51, line 65 through column 52, line 50

"

| Gelatin Overcoat |
|---|
| Ultraviolet Protective Overcoat |
| Fast blue-sensitive, yellow-dye-forming silver halide emulsion layer. Blue-sensitive AgX as Ag - 0.93. Yellow coupler (see Example 2) - 0.30 in di-n-butyl phthalate - 0.10; Gelatin - 0.61 |
| Slow blue-sensitive, yellow dye-forming silver halide emulsion layer, Blue-sensitive AgX as Ag - 0.62. Yellow coupler (see Example 2) - 1.25 in di-n-butyl phthalate - 0.42; Gelatin - 1.99 |
| Yellow Colloidal Silver Filter Layer |

"

UNITED STATES PATENT OFFICE
CERTIFICATE OF CORRECTION

Patent No. 4,248,962  Dated February 3, 1981

Inventor(s) Philip T. S. Lau

It is certified that error appears in the above-identified patent and that said Letters Patent are hereby corrected as shown below:

Column 51, line 65 through column 52, line 50 (continued)

"
Fast green-sensitive magenta-dye-forming silver halide emulsion layer. Green-sensitive AgX as Ag - 1.23. Magenta coupler (see below) - 0.098 in tricresylphosphate - 0.098. Colored magenta coupler (see below) - 0.03 in tricresylphosphate - 0.03. Gelatin - 0.63

Slow green-sensitive magenta-dye-forming silver halide emulsion layer. Green-sensitive AgX as Ag - 1.49. Magenta coupler (see below) - 0.59 in tricresylphosphate - 0.59. Colored magenta coupler (see below) - 0.092 in tricresylphosphate - 0.092. Magenta DIR coupler (see below) - 0.019 in tricresylphosphate - 0.019. Gelatin - 1.25

Gelatin Interlayer

Fast red-sensitive cyan-dye-forming silver halide emulsion layer. Red-sensitive AgX as Ag - 1.31. Cyan coupler (see Example 1) - 0.097 in di-n-butyl phthalate - 0.48. Colored cyan coupler (see below) - 0.004 in di-n-butyl phthalate - 0.002. Gelatin - 0.61

Slow red-sensitive cyan-dye-forming silver halide emulsion layer. Red-sensitive AgX as Ag - 2.26. Cyan coupler (see Example 1) - 0.59 in di-n-butyl phthalate - 0.29. Colored cyan coupler (see below) - 0.053 in di-n-butyl phthalate - 0.027. DIR coupler (see below). Gelatin - (see below)

Antihalation layer

Film Support
"

should read

UNITED STATES PATENT OFFICE
CERTIFICATE OF CORRECTION

Patent No. 4,248,962      Dated February 3, 1981

Inventor(s) Philip T. S. Lau

It is certified that error appears in the above-identified patent and that said Letters Patent are hereby corrected as shown below:

Column 51, line 65 through column 52, line 50 (continued)

--- ---.

| |
|---|
| Gelatin Overcoat |
| Ultraviolet Protective Overcoat |
| Fast blue-sensitive, yellow-dye-forming silver halide emulsion layer. Blue-sensitive AgX as Ag - 0.93. Yellow coupler (see Example 2) - 0.30 in di-n-butyl phthalate - 0.10; Gelatin - 0.61 |
| Slow blue-sensitive, yellow dye-forming silver halide emulsion layer. Blue-sensitive AgX as Ag - 0.62. Yellow coupler (see Example 2) - 1.25 in di-n-butyl phthalate - 0.42. Gelatin - 1.99 |
| Yellow Colloidal Silver Filter Layer |
| Fast green-sensitive magenta-dye-forming silver halide emulsion layer. Green-sensitive AgX as Ag - 1.23. Magenta coupler (see below) - 0.098 in tricresylphosphate - 0.098. Colored magenta coupler (see below) - 0.03 in tricresylphosphate - 0.03. Gelatin - 0.63 |
| Slow green-sensitive magenta-dye-forming silver halide emulsion layer. Green-sensitive AgX as Ag - 1.49. Magenta coupler (see below) - 0.59 in tricresylphosphate - 0.59. Colored magenta coupler (see below) - 0.092 in tricresylphosphate - 0.092. Magenta DIR coupler (see below) - 0.019 in tricresylphosphate - 0.039; Gelatin - 1.25 |
| Gelatin Interlayer |
| Fast red-sensitive cyan-dye-forming silver halide emulsion layer; Red-sensitive AgX as Ag - 1.31; Cyan coupler (see Example 1) - 0.097 in di-n-butyl phthalate - 0.48; Colored cyan coupler (see below) - 0.004 in di-n-butyl phthalate - 0.002; Gelatin - 0.61 |

UNITED STATES PATENT OFFICE
CERTIFICATE OF CORRECTION

Patent No. 4,248,962  Dated February 3, 1981

Inventor(s) Philip T. S. Lau

It is certified that error appears in the above-identified patent and that said Letters Patent are hereby corrected as shown below:

Column 51, line 65 through column 52, line 50 (continued)

| |
|---|
| Slow red-sensitive cyan-dye-forming silver halide emulsion layer. Red-sensitive AgX as Ag - 2.26, Cyan coupler (see Example 1) - 0.59 in di-n-butyl phthalate - 0.29, Colored cyan coupler (see below) - 0.053 in di-n-butyl phthalate - 0.027; DIR coupler (see below); Gelatin - (see below) |
| Antihalation layer |
| Film Support |

Column 54, lines 1-12

"
| |
|---|
| Gelatin |
| Green-sensitive AgX gelatino emulsion layer containing a DIR coupler in 2 parts by weight of diethyl lauramide and a cyan-dye-forming coupler or a magenta-dye-forming coupler in ½ part by weight of di-n-butyl phthalate |
| Interlayer |
| Red-sensitive AgX gelatino emulsion layer containing a yellow dye forming coupler in ½ part by weight of di-n-butyl phthalate |
| Film Support |
"

should be

| |
|---|
| Gelatin |
| Green-sensitive AgX gelatino emulsion layer containing a DIR coupler in 2 parts by weight of diethyl lauramide and a cyan-dye-forming coupler or a magenta-dye-forming coupler in ½ part by weight of di-n-butyl phthalate |
| Interlayer |
| Red-sensitive AgX gelatino emulsion layer containing a yellow dye forming coupler in ½ part by weight of di-n-butyl phthalate |
| Film Support |

UNITED STATES PATENT OFFICE
CERTIFICATE OF CORRECTION

Patent No. 4,248,962   Dated February 3, 1981

Inventor(s) Philip T. S. Lau

It is certified that error appears in the above-identified patent and that said Letters Patent are hereby corrected as shown below:

Column 54, line 67, "means" should be ---group--- and

Column 59, line 22, "photographically useful groups" should be ---photographic dye or reagent---.

Signed and Sealed this

Sixteenth Day of June 1981

[SEAL]

Attest:

RENE D. TEGTMEYER

Attesting Officer    Acting Commissioner of Patents and Trademarks